US009809864B2

(12) United States Patent
Preston et al.

(10) Patent No.: US 9,809,864 B2
(45) Date of Patent: Nov. 7, 2017

(54) DUAL SEQUENCE-CAPTURE METHOD FOR QUANTIFYING TRANS RENAL HPV DNA IN URINE

(71) Applicant: THE JOHNS HOPKINS UNIVERSITY, Baltimore, MD (US)

(72) Inventors: Rafael Guerrero Preston, Baltimore, MD (US); Anne Jedlicka, Fallston, MD (US); David Sidransky, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/772,004

(22) PCT Filed: Mar. 3, 2014

(86) PCT No.: PCT/US2014/019934
§ 371 (c)(1),
(2) Date: Sep. 1, 2015

(87) PCT Pub. No.: WO2014/134607
PCT Pub. Date: Sep. 4, 2014

(65) Prior Publication Data
US 2016/0010163 A1    Jan. 14, 2016

Related U.S. Application Data

(60) Provisional application No. 61/771,462, filed on Mar. 1, 2013.

(51) Int. Cl.
*C12Q 1/70* (2006.01)
*C12Q 1/68* (2006.01)

(52) U.S. Cl.
CPC .......... *C12Q 1/708* (2013.01); *C12Q 1/6806* (2013.01); *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS 6,482,588 B1   11/2002   Van Doorn et al.
7,393,633 B1    7/2008   Park et al.

FOREIGN PATENT DOCUMENTS

WO        2006-038753 A1    4/2006

OTHER PUBLICATIONS

Bianchi, et al. (2013) "Detection and Genotyping of Human Papillomavirus in Urine Samples from Unvaccinated Male and Female Adolescents in Italy", PLoS One, 8(11): e79719 (pp. 1-6).*
Schuh, "Trovagene Transrenal Molecular Diagnostics, Introduction to Trovagene, Inc.", Published online by Trovagene, San Diego, CA, USA, Nov. 6, 2012, 17 pages long.*
Benson D.A.; Karsch-Mizrachi I.; Lipman D.J.; Ostell J.; Sayers E.W. (2009). GenBank. Nucleic Acids Res. Jan. 2009;37(Database issue):D26-31. Epub Oct. 21, 2008.
Beaudenon, S.; Huibregtse, J. M., HPV E6, E6AP and cervical cancer. BMC Biochem 9 Suppl 1, S4 (2008).
Blanchette, M.; Kent, W.J.; Riemer, C.; Elnitski, L.; Smit, A.F.; Roskin, R.M.; Baertsch, R.; Rosenbloom, K.; Clawson, H.; Green, E.D.; Haussler, D.; Miller, W. (2004) Aligning multiple genomic sequences with the threaded blockset aligner, Genome Res. 14(4), 708-15.
Brown, A.J. and C.L. Trimble, New technologies for cervical cancer screening. Best Pract Res Clin Obstet Gynaecol, 2012. 26(2): p. 233-42.
Cuschieri, K.S.; Whitley, M. J.; Cubie, H. A. Human papillomavirus type specific DNA and RNA persistence—implications for cervical disease progression and monitoring. J Med Virol 2004.73, 65.
Dehn, D.; Torkko, K.C.; Shroyer, K. R. Human papillomavirus testing and molecular markers of cervical dysplasia and carcinoma. Cancer 2007. 111, 1.
Dillner, J.; Rebolj, M.; Birembaut, P.; Petry, K.-U.; Szarewski, A.; Munk, C.; de Sanjose, S.; Naucler, P.; Lloveras, B.; Kjaer, S.; Cuzick, J.; van Ballegooijen, M.; Clavel, C.; Iftner, T.; Long term predictive values of cytology and human papillomavirus testing in cervical cancer screening: joint European cohort study. BMJ, 2008. 337: p. a1754.
Doorbar, J., Molecular biology of human papillomavirus infection and cervical cancer. Clin Sci (Lond), 2006. 110(5): p. 525-41.
Eberharter, A. and P. B. Becker, Histone acetylation: a switch between repressive and permissive chromatin. Second in review series on chromatin dynamics. EMBO Rep, 2002. 3(3): p. 224-9.
Esteller, M. Epigenetics provides a new generation of oncogenes and tumour-suppressor genes. Br J Cancer, 2006. 94(2): p. 179-83.
Florea, L.; McClelland, M.; Riemer, C.; Schwartz, S. and Miller, W. Enterix 2003: Visualization Tools for Genome Alignments of Enterobacteriaceae, Nucl. Acids Res. 2003. 31(13), 3527-32.
Kjaer, S. K.; van den Brule, A. J. C.; Paull, G.; Svare, E. I.; Sherman, M. E.; Thomsen, B. L.; Suntum, M.; ; Bock, J. E.; ; Poll, P. A.; Meijer, C. J. L.M. Type specific persistence of high risk human papillomavirus (HPV) as indicator of high grade cervical squamous intraepithelial lesions in young women: population based prospective follow up study. BMJ 2002. 325, 572.
Melkonyan, H.S., Feaver, W. J.; Meyer, E.; Scheinker, V.; Shekhtman, E. M.; Xin, Z.; Umansky, S. R. Transrenal nucleic acids: from proof of principle to clinical tests. Ann N Y Acad Sci, 2008. 1137: p. 73-81.
Monsonego, J.; Bosch, F.X.; Coursaget, P.; Cox, Franco, E.; Frazer, I.; Sankaranarayanan, R.; Schiller, J.; Singer, A.; Wright, T.C. Jr.; Kinney, W.; Meijer, C. J.; Linder, J.; McGoogan, E.; Meijer, C. Cervical cancer control, priorities and new directions. Int J Cancer 2004. 108, 329.

(Continued)

*Primary Examiner* — Robert M Kelly
(74) *Attorney, Agent, or Firm* — John Hopkins Technology Transfer

(57) ABSTRACT

Methods for the quantifying HPV Trans Renal DNA (TrDNA) from a urine sample from a subject using a dual sequence-capture approach are disclosed. The presently disclosed methods can be used to predict cancers including, but not limited to, cervical, anal, penile, and oropharyngeal cancers.

15 Claims, 15 Drawing Sheets

(56) References Cited

OTHER PUBLICATIONS

Sasagawa, T., [Updated cervical cancer screening; human papilloma virus and Papanicolaou tests]. Rinsho Byori, 2009. 57(9): p. 905-12.
Saslow, D.; Solomon, D.; Lawson, H. W.; Killackey, M.; Kulasingam, S. L.; Cain, J.; Garcia, F. A. R.; Moriarty, A. T.; Waxman, A. G. Wilbur, D. C.; Wentzensen, N.; Downs, L. S.; Spitzer, M.; Moscicki, A.-B.; Franco, E.-L.; Stoler, M.-H.; Schiffman, M.; Castle, P. E.; Myers, E. R.; American Cancer Society, American Society for Colposcopy and Cervical Pathology, and American Society for Clinical Pathology screening guidelines for the prevention and early detection of cervical cancer. CA Cancer J Clin 2012. 62(3): p. 147-72.
Sayers E.W.; Barrett, T.; Benson D.A.; Bryant S.H.; Canese K.; Chetvernin V.;Church D.M.; DiCuccio M.; Edgar R.; Federhen S.; Feolo M.; Geer L.Y.; Helmberg W.; Kapustin Y.; Landsman D.; Lipman D.J.; Madden T.L.; Maglott D.R.; Miller V.; Mizrachi I.; Ostell J.; Pruitt K.D.; Schuler G.D.; Sequeira E.; Sherry S.T.; Shumway M.; Sirotkin K.; Souvorov A.; Starchenko G.; Tatusova T.A.; Wagner L.; Yaschenko E.; Ye J. (2009). Database resources of the National Center for Biotechnology Information. Nucleic Acids Res. Jan. 2009;37(Database issue):D5-15. Epub Oct. 21, 2008.
Schwartz, S.; Kent, W.J.; Smit, A. ; Zhang, Z.; Baertsch, R.; Hardison, R.C.; Haussler, D.; Miller, W. Human-Mouse Alignments with Blastz, Genome Res. 2003. 3(1), 103-7.
Schwartz, S.; Zhang, Z.; Frazer, K.A.; Smit, A.; Riemer, C.; Bouck, J.; Gibbs, R.; Hardison, R.; W. Miller, W. PipMaker—A web server for aligning two genomic DNA sequences, Genome Res. 2000. 10(4), 577-86.
Studnicki, J., Berndt, D. J. Luther, S. L.; Fisher, J. W.; van Caulil, K.; Brennan, M. J.; Martinez, Y. G.; Clarke, P. Hispanic health status in Orange County, Florida. J Public Health Manag Pract 2005. 11(4): p. 326-32.
Tycko, B., Epigenetic gene silencing in cancer. J Clin Invest 2000. 105(4): p. 401-7.
Walenz, B., Florea, L. Sim4db and leaff: Utilities for fast batch spliced alignment and sequence indexing, Bioinformatics 2011. 27(13):1869-70.
Woodman, C.B., Collins, S. I.; Young, L. S. The natural history of cervical HPV infection: unresolved issues. Nat Rev Cancer 2007. 7(1): p. 11-22.
International Search Report and Written Opinion dated Jun. 27, 2014 from PCT International Application No. PCT/US14/19934.
Enk, M. J., et al., "Diagnostic accuracy and applicability of a PCR system for the detection of Schistosoma mansoni DNA in human urine samples from an endemic area," PLos One, vol. 7, Issue 6, Article No. e38947, pp. 1-6 (Jun. 2012).
Carozzi, F., et al., "Agreement between the AMPLICOR human papillomavirus test and the hybrid capture 2 assay in detection of high-risk human papillomavirus and diagnosis of biopsy-confirmed high-grade cervical disease," Journal of Clinical Microbiology, vol. 45, No. 2, pp. 364-369 (Feb. 2007).
Umansky, S.R., et al., "Transrenal DNA testing; progress and perspectives," Expert review of Molecular Diagnostics, vol. 6, No. 2, pp. 153-163 (Mar. 2006).

\* cited by examiner

TrDNA-445: MULTIPLE ALIGNMENT RESULTS

| READS | HUMAN PAPILLOMAVIRUS TYPE |
|---|---|
| 1 | HUMAN PAPILLOMAVIRUS TYPE 56 CLONE QV24970, COMPLETE GENOME |
| 20 | HUMAN PAPILLOMAVIRUS TYPE 45 ISOLATE QV31035, COMPLETE GENOME |
| 1 | HUMAN PAPILLOMAVIRUS TYPE 72 |
| 743 | HUMAN PAPILLOMAVIRUS TYPE 18 COMPLETE SEQUENCE |
| 24846 | HUMAN PAPILLOMAVIRUS TYPE 16, COMPLETE GENOME |
| 2 | HUMAN PAPILLOMAVIRUS TYPE 31 ISOLATE QV12357, GENOME |
| 1 | HUMAN PAPILLOMAVIRUS TYPE 35 ISOLATE QV29782, COMPLETE GENOME |
| 4 | HUMAN PAPILLOMAVIRUS TYPE 59, COMPLETE VIRAL GENOME |
| 380 | UNMAPPED |

MOST OF THE CONTIGS CONTAIN MAPS TO 16 AND 18, WITH VERY FEW UNMAPPED READS.

TrDNA-456: MULTIPLE ALIGNMENT RESULTS

| READS | HUMAN PAPILLOMAVIRUS TYPE |
|---|---|
| 193 | HUMAN PAPILLOMAVIRUS TYPE 44, COMPLETE GENOME |
| 24 | HUMAN PAPILLOMAVIRUS TYPE 61, COMPLETE GENOME |
| 841 | HUMAN PAPILLOMAVIRUS TYPE 56 CLONE QV24970, COMPLETE GENOME |
| 243 | HUMAN PAPILLOMAVIRUS TYPE 45 ISOLATE QV31035, COMPLETE GENOME |
| 231 | HUMAN PAPILLOMAVIRUS TYPE 72 |
| 109 | HUMAN PAPILLOMAVIRUS TYPE 11 ISOLATE LZod45-11, COMPLETE GENOME |
| 837 | HUMAN PAPILLOMAVIRUS TYPE 42 ISOLATE TJ43-42, COMPLETE GENOME |
| 54 | HUMAN PAPILLOMAVIRUS TYPE 53 ISOLATE TJ43-53, COMPLETE GENOME |
| 493 | HUMAN PAPILLOMAVIRUS TYPE 18 COMPLETE SEQUENCE |
| 732 | HUMAN PAPILLOMAVIRUS TYPE 16, COMPLETE GENOME |
| 421 | HUMAN PAPILLOMAVIRUS TYPE 68b, COMPLETE GENOME |
| 226 | HUMAN PAPILLOMAVIRUS TYPE 6 COMPLETE GENOME, ISOLATE CAC231 |
| 156 | HUMAN PAPILLOMAVIRUS TYPE 39 |
| 330 | HUMAN PAPILLOMAVIRUS TYPE 31 ISOLATE QV12358, COMPLETE GENOME |
| 10060 | HUMAN PAPILLOMAVIRUS TYPE 33 ISOLATE QV34189, COMPLETE GENOME |
| 564 | HUMAN PAPILLOMAVIRUS TYPE 35 ISOLATE QV29782, COMPLETE GENOME |
| 145 | HUMAN PAPILLOMAVIRUS TYPE 52 ISOLATE QV03594, COMPLETE GENOME |
| 1533 | HUMAN PAPILLOMAVIRUS TYPE 58 ISOLATE Z094, COMPLETE GENOME |
| 184 | HUMAN PAPILLOMAVIRUS TYPE 81 COMPLETE GENOME |
| 17645 | HUMAN PAPILLOMAVIRUS TYPE 59, COMPLETE VIRAL GENOME |
| 48 | HUMAN PAPILLOMAVIRUS TYPE 54, COMPLETE GENOME |
| 10913 | UNMAPPED |

FIG. 10

DUAL SEQUENCE-CAPTURE METHOD FOR QUANTIFYING TRANS RENAL HPV DNA IN URINE

CROSS REFERENCE TO RELATED APPLICATIONS

This application is a 35 U.S.C. §371 National Stage Entry of International Application No. PCT/US2014/019934 having an international filing date of Mar. 3, 2014, which claims the benefit of U.S. Provisional Application No. 61/771,462, filed Mar. 1, 2013, the content of each of the aforementioned applications is incorporated herein by reference in its entirety.

FEDERALLY SPONSORED RESEARCH OR DEVELOPMENT

This invention was made in part with United States Government support under 151866, 151628, 5U01CA13-8, and K01CA164092 awarded by the National Cancer Institute (NCI). The U.S. Government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00445_ST25.txt". The sequence listing is 2,606 bytes in size, and was created on Sep. 1, 2015. It is hereby incorporated by reference in its entirety.

BACKGROUND

Cervical cancer, the second most prevalent cancer in women and the fifth cause of death by cancer among women worldwide, is a considerable public health problem. Human papillomavirus (HPV) is the etiologic agent for the vast majority of cervical dysplasia and carcinoma (Dehn et al., 2007). Around 470,000 new cases of cervical cancer are detected annually, mostly in developing nations, of which approximately half of those diagnosed with cervical cancer will die (Beaudenon and Huibregtse, 2008).

Because cervical cancer develops slowly, early detection can lead to a 90-100% cure rate. Papanicolaou smear (Pap smear) screening, a test that only has 50-60% sensitivity, has decreased cervical cancer mortality in the United States and Europe four- to five-fold. Cultural differences and medical infrastructure limitations have limited the successful implementation of Pap smear screening in developing countries.

The intensive medical infrastructure required by and the low sensitivity of the Pap smear test has stimulated searches for other cervical cancer screening techniques. Also, although cervical cytology is a highly effective screening test for cancer, it has limited specificity for clinically significant lesions in cases with low-grade cytologic abnormalities. Up to a quarter of all patients tested may have a false-negative result on the basis of cervical cytology testing alone (Sasagawa, 2009).

Cervical cancer is caused by infection with high-risk HPV, making it a target for screening. HPV testing has been adopted for the triage of patients after a cervical cytology screening test (Pap smear or liquid-based cervical cytology such as ThinPrep or SurePath) interpretation of atypical squamous cells of undetermined significance (ASCUS), and HPV testing is increasingly used for screening in conjunction with cervical cytology (Woodman et al., 2007; Dillner et al., 2008; Saslow et al., 2012). These screening programs are inefficient at identifying individuals at risk for disease, requiring multiple visits over a women's lifetime, which is costly and cumbersome (Brown and Trimble, 2012). Currently, there is a growing interest to switch screening for cervical cancer from Pap smears to more sensitive and cost-effective detection of high-risk HPV. There is also great interest in identifying molecular markers of progression that can identify which patients with high risk HPV and abnormal Pap smears will progress to cervical cancer.

Privacy, cultural and infrastructure issues challenge the effective implementation of cervical cytology and HPV screening for millions of women world-wide. In addition, the projected loss in the Positive Predictive Value (PPV) of cytology in the post vaccination era suggests a need to rely on molecular markers of HPV infection and technologies, such as HPV genotyping, for the new generation of cervical cancer screening, preventive and targeted therapeutics technologies. Furthermore, the United States Food and Drug Administration approval of HPV genotyping tests has led to questions about how typing can assist cervical cancer screening and personalized clinical decisions in a cost-effective manner.

SUMMARY

The presently disclosed subject matter provides methods for detecting HPV Trans-Renal DNA (TrDNA) from urine. In some aspects, the presently disclosed methods comprise using a solution-based capture approach to detect high-risk HPV-TrDNA.

Accordingly, in one aspect, the presently disclosed subject matter provides a sequence-based method for detecting HPV Trans-Renal DNA (TrDNA) in a subject, the method comprising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises: (i) preparing a library of the low molecular weight, fragmented cell-free nucleic acids; (ii) amplifying the library using PCR to form a pre-capture PCR library; (iii) hybridizing the pre-capture PCR library to a custom-designed pool of HPV-specific capture probes to form a post-capture PCR library; (iv) amplifying the post-capture PCR library to produce one or more enriched HPV TrDNA; and (v) optionally repeating steps (iii) and (iv); (d) adding at least one index to the one or more enriched HPV TrDNA; (e) performing multiplexed sequencing of the one or more enriched HPV TrDNA having at least one index added thereto to produce a multiplexed nucleotide sequence; (f) performing a sequence alignment between the multiplexed nucleotide sequence and the nucleotide sequence of one or more known HPV genotypes; and (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject.

In another aspect, the presently disclosed subject matter provides a method for predicting or screening for cancer by detecting HPV Trans-Renal DNA (TrDNA) in a subject, the method comprising steps (a)-(g) provided immediately hereinabove, wherein at least a 60% sequence identity between the multiplexed nucleotide sequence and the nucleotide sequence of the one or more known high-risk HPV genotypes is indicative that the subject has or is at risk for developing a cancer.

In still another aspect, the presently disclosed subject matter provides a sequence-based method for detecting methylated HPV Trans-Renal DNA (TrDNA) in a subject, the method comprising steps (a)-(g) provided hereinabove, wherein prior to step (d) the post-capture library is treated with a bisulfate compound and is amplified using PCR to form one or more amplified methylated HPV TrDNA; and further wherein at least a 70% sequence identity between the multiplexed nucleotide sequence and the nucleotide sequence of the one or more known methylated HPV genotypes means that methylated HPV TrDNA has been detected in the subject.

In a further aspect, the presently disclosed subject matter provides a method for predicting or screening for cancer by detecting methylated HPV Trans-Renal DNA (TrDNA) in a subject, the method comprising steps (a)-(g) provided hereinabove, wherein prior to step (d) the post-capture library is treated with a bisulfite compound and is amplified using PCR to form one or more amplified methylated HPV TrDNA; and further, wherein at least a 70% sequence identity between the multiplexed nucleotide sequence and the nucleotide sequence of the one or more known high-risk methylated HPV genotypes is indicative that the subject has or is at risk for developing a cancer.

In particular aspects, the cancer is selected from the group consisting of cervical, anal, penile, and oropharyngeal cancers.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
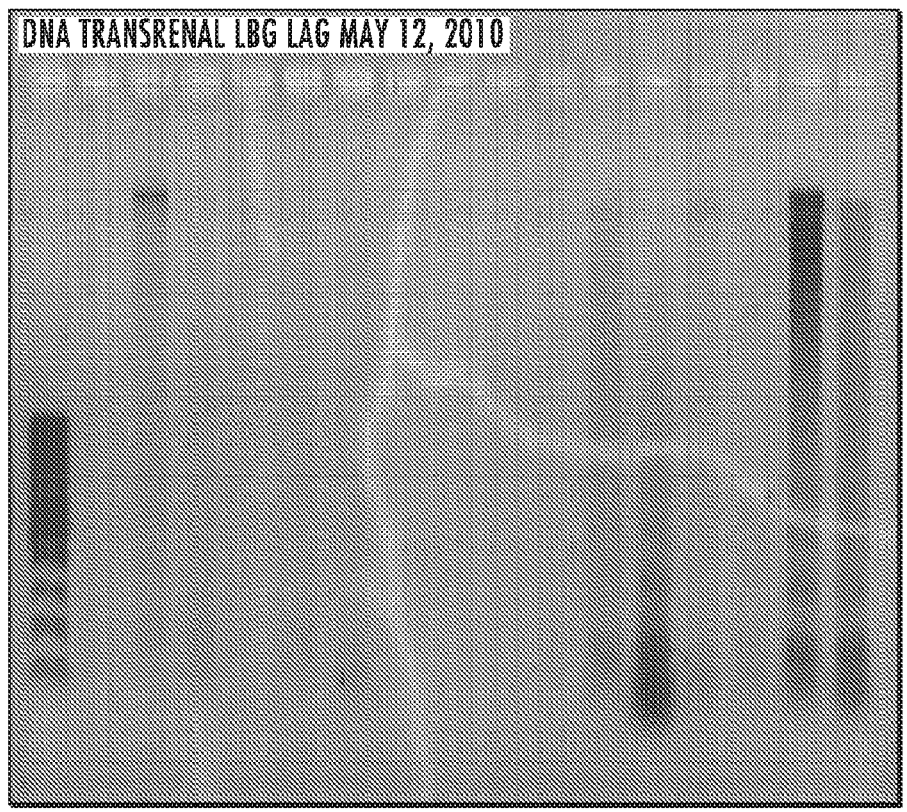
Figure 1B:
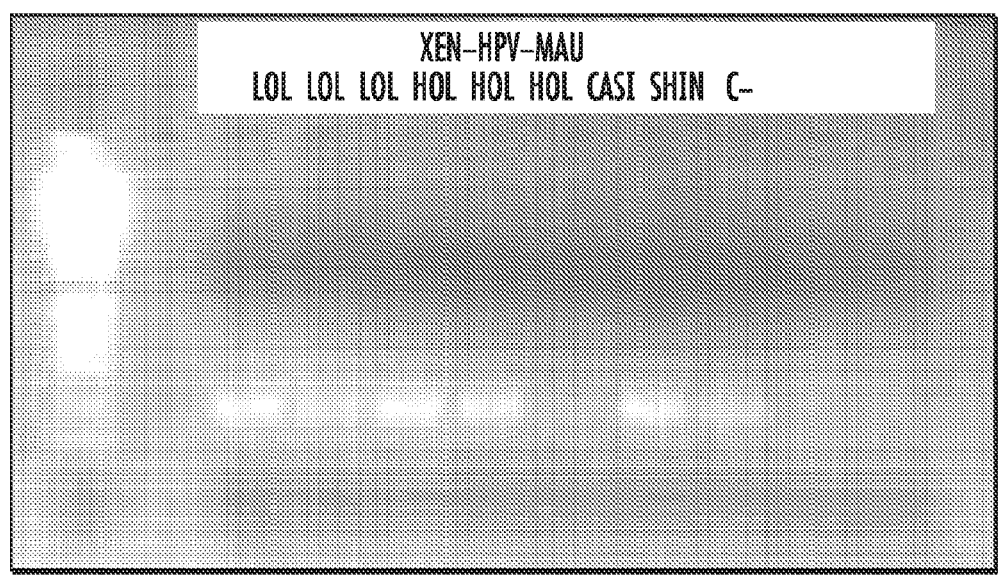
Figure 2A:
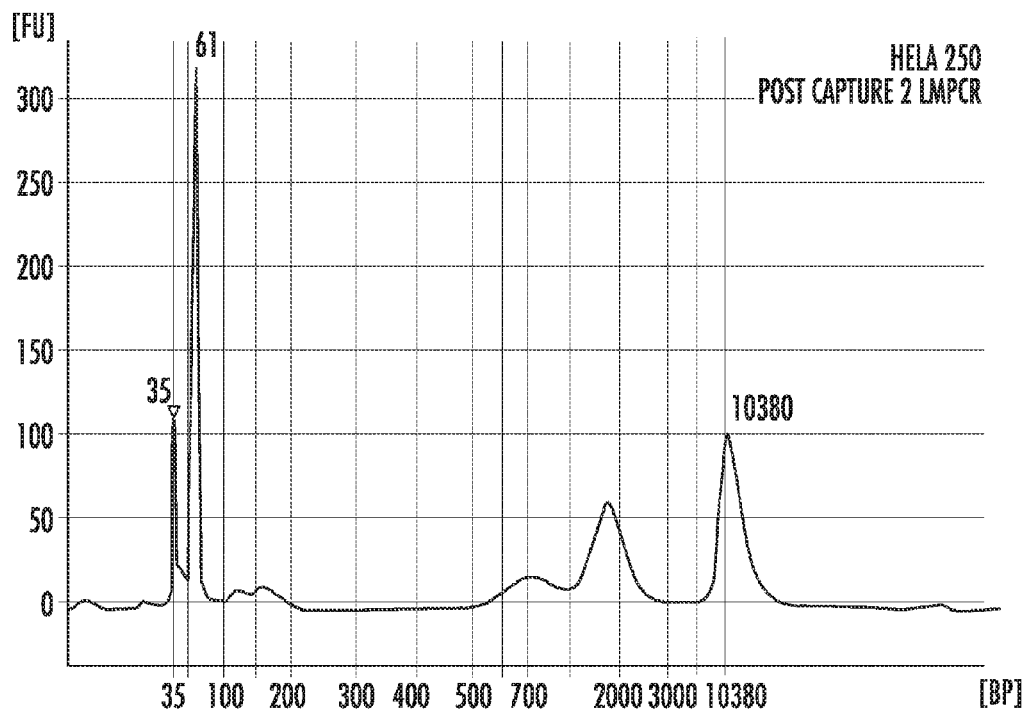
Figure 2B:
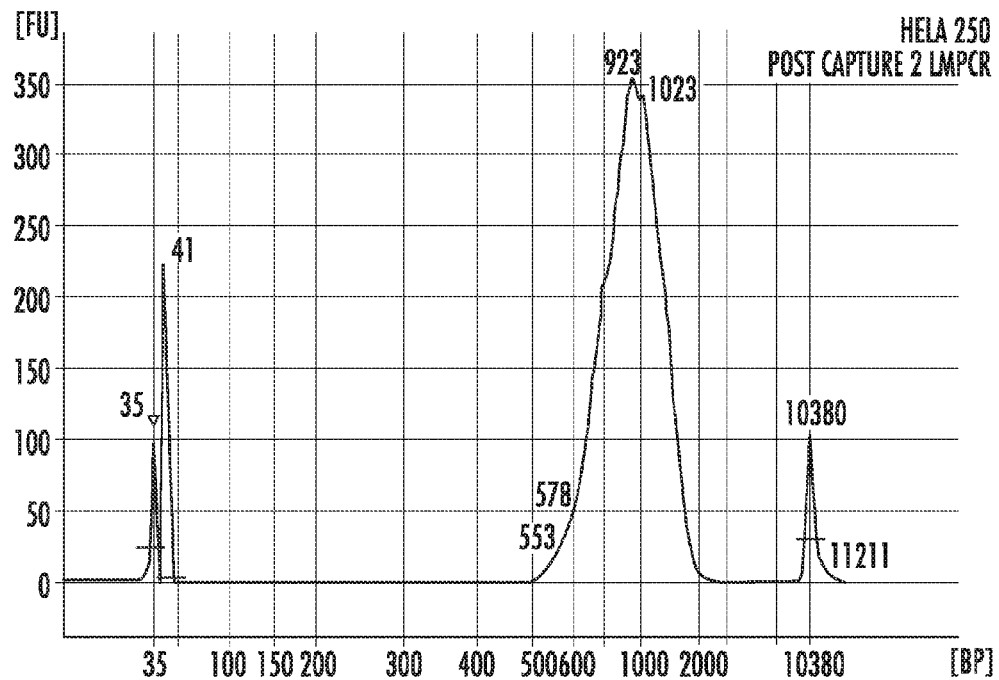
Figure 3:
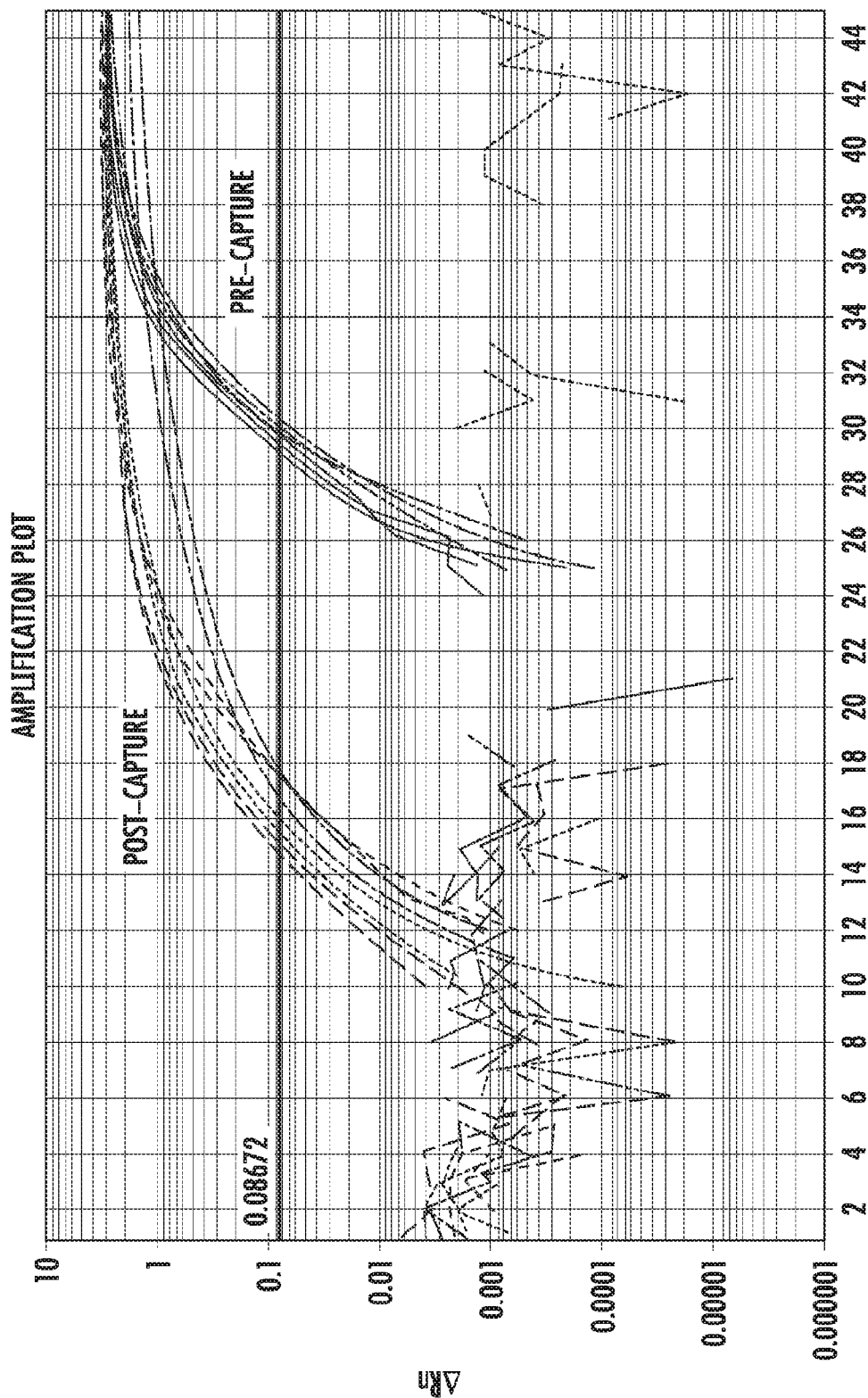
Figure 4A:
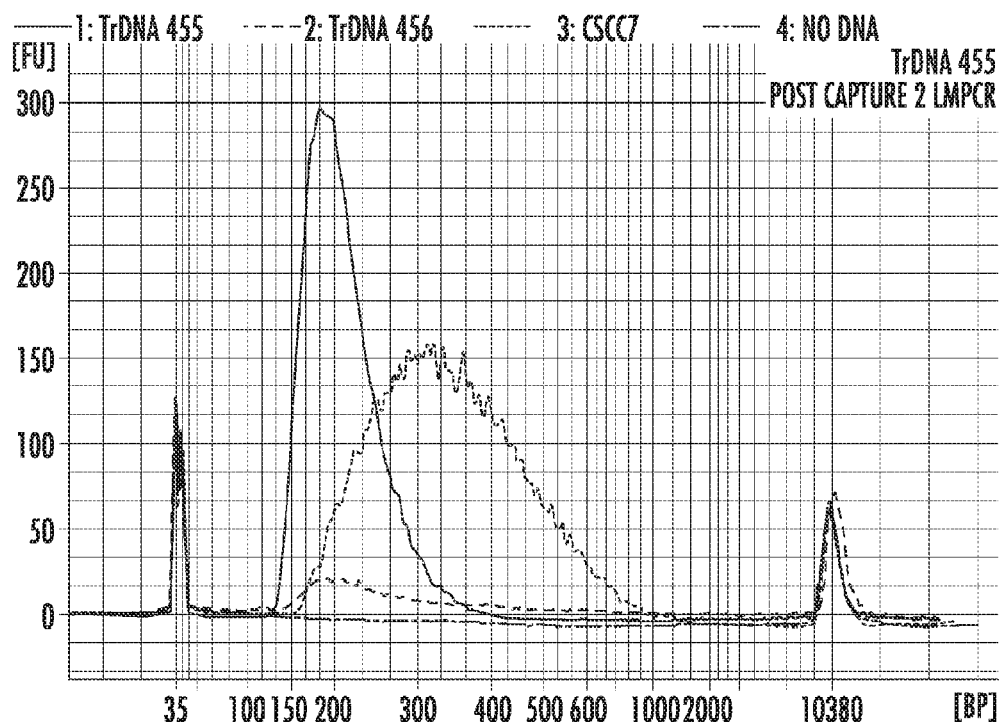
Figure 4B:
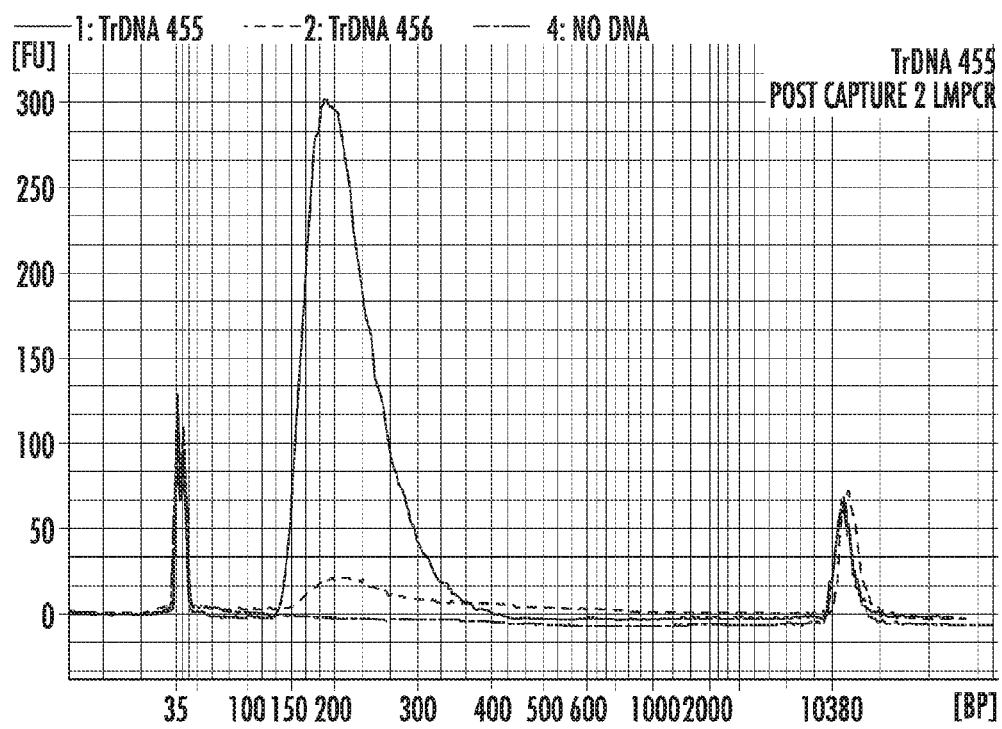
Figure 5:
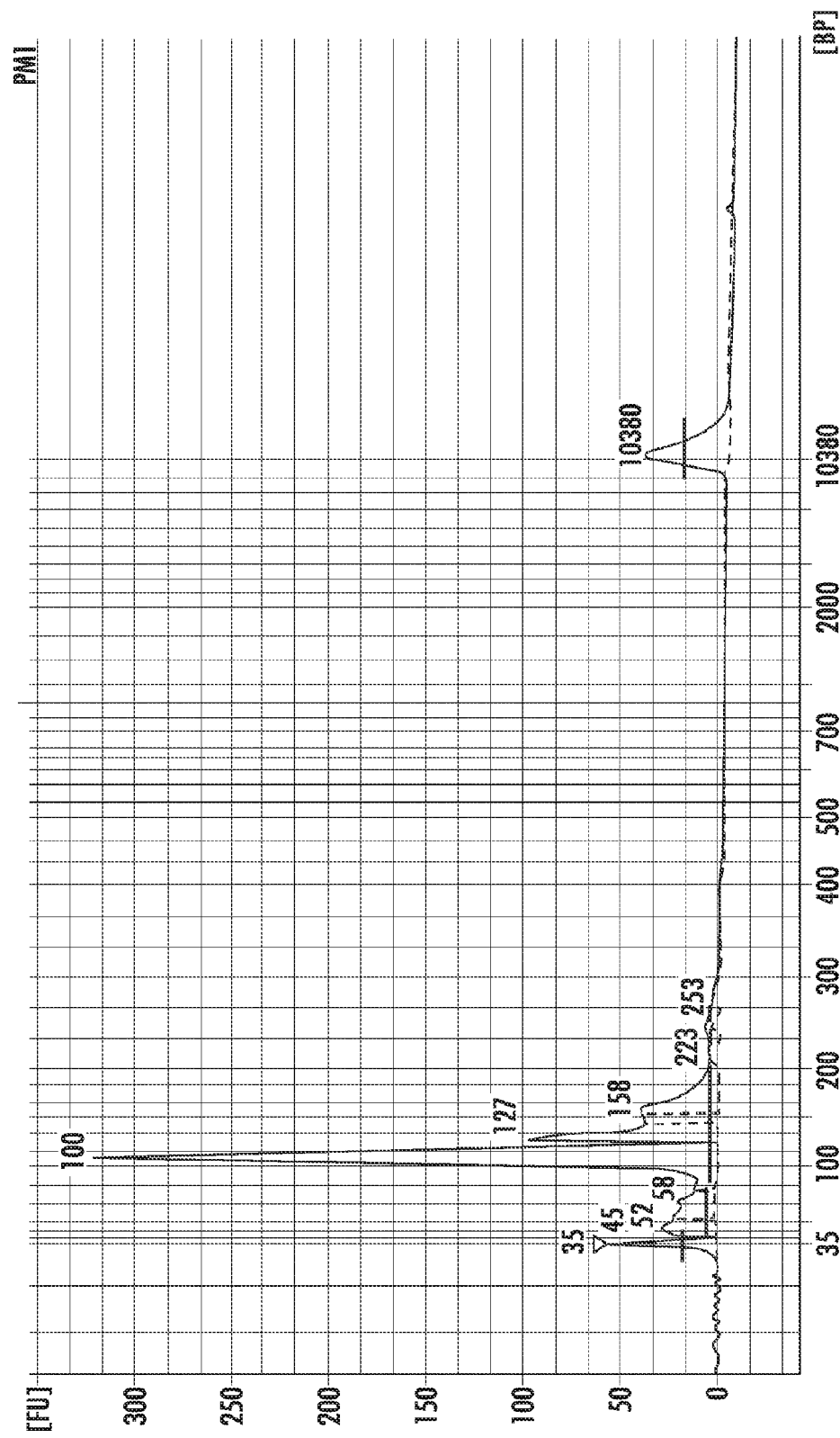
Figure 6:
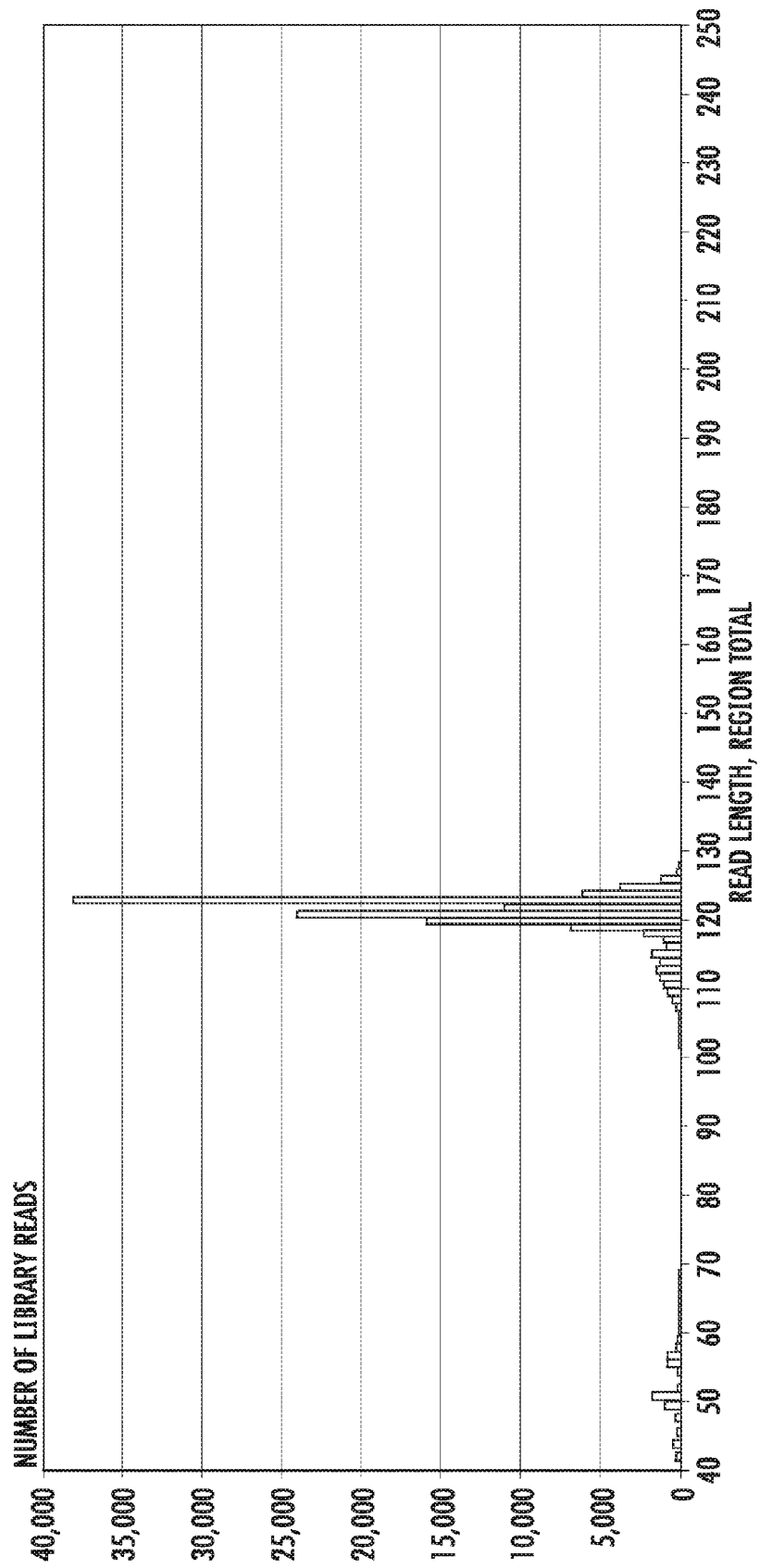
Figure 7A:
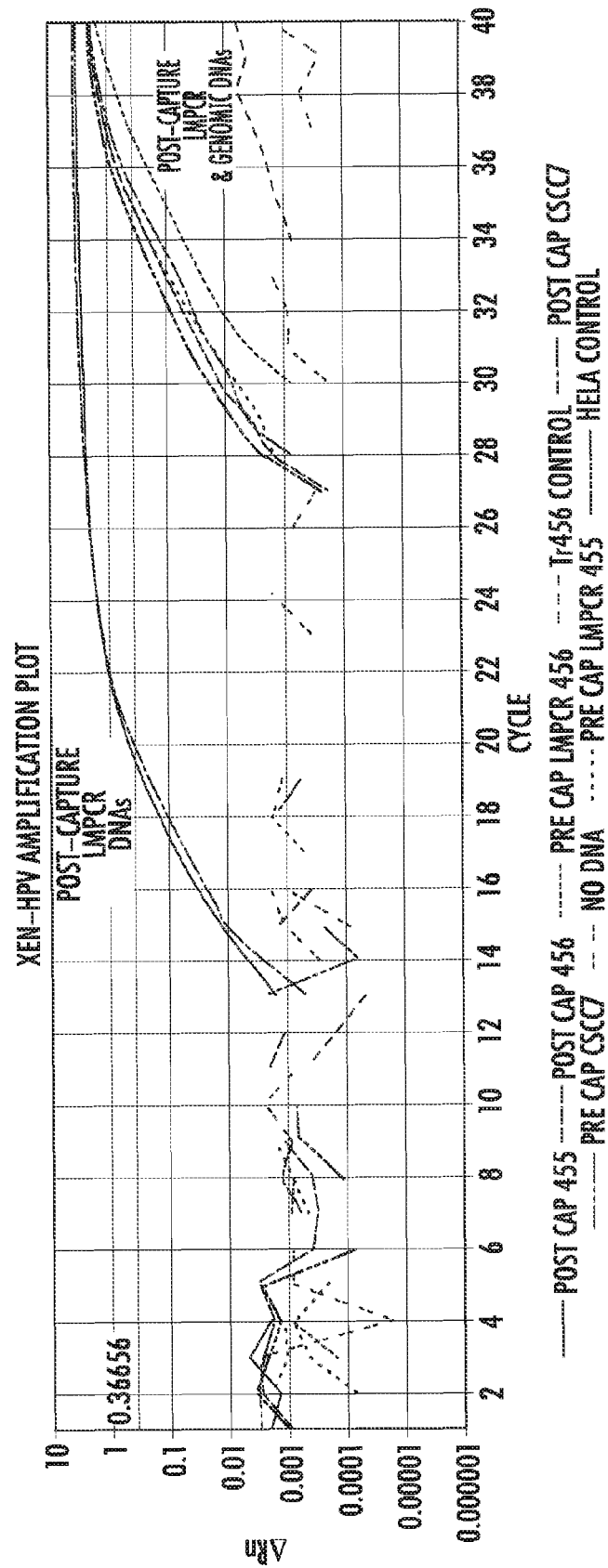
Figure 7B:
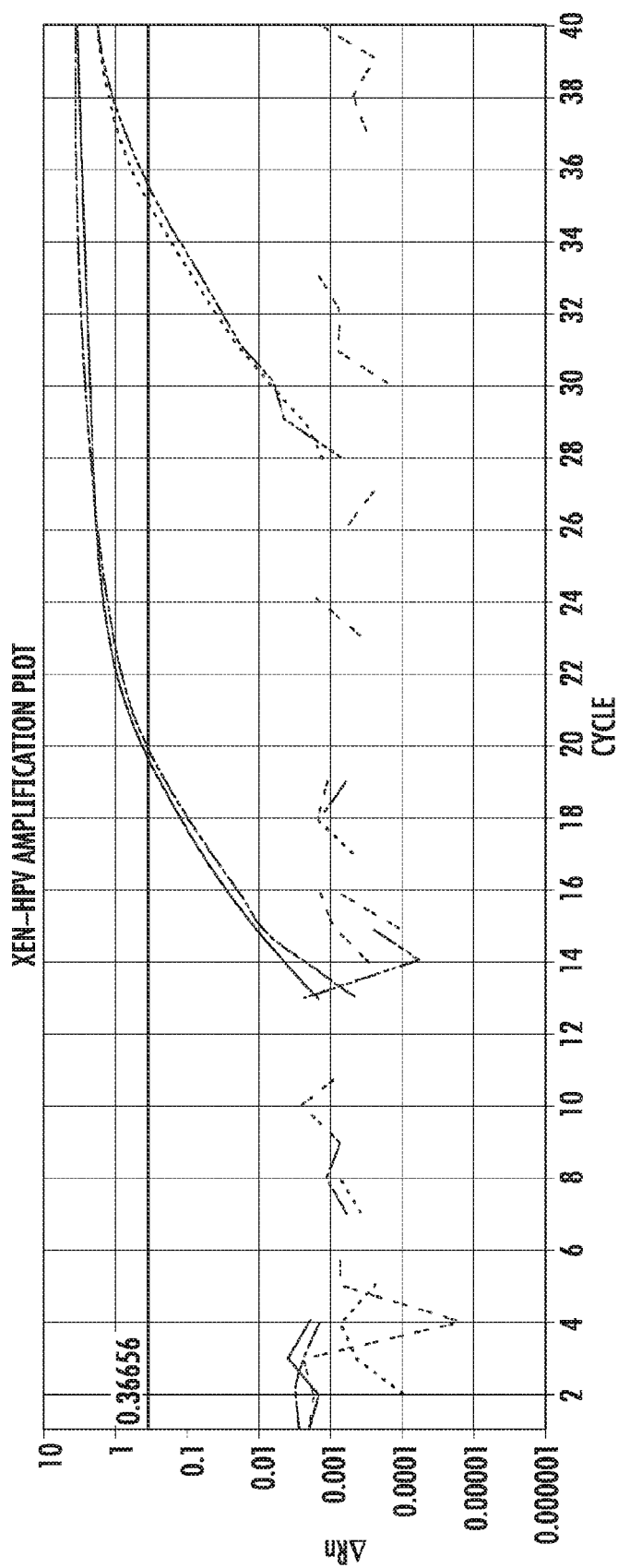
Figure 8:
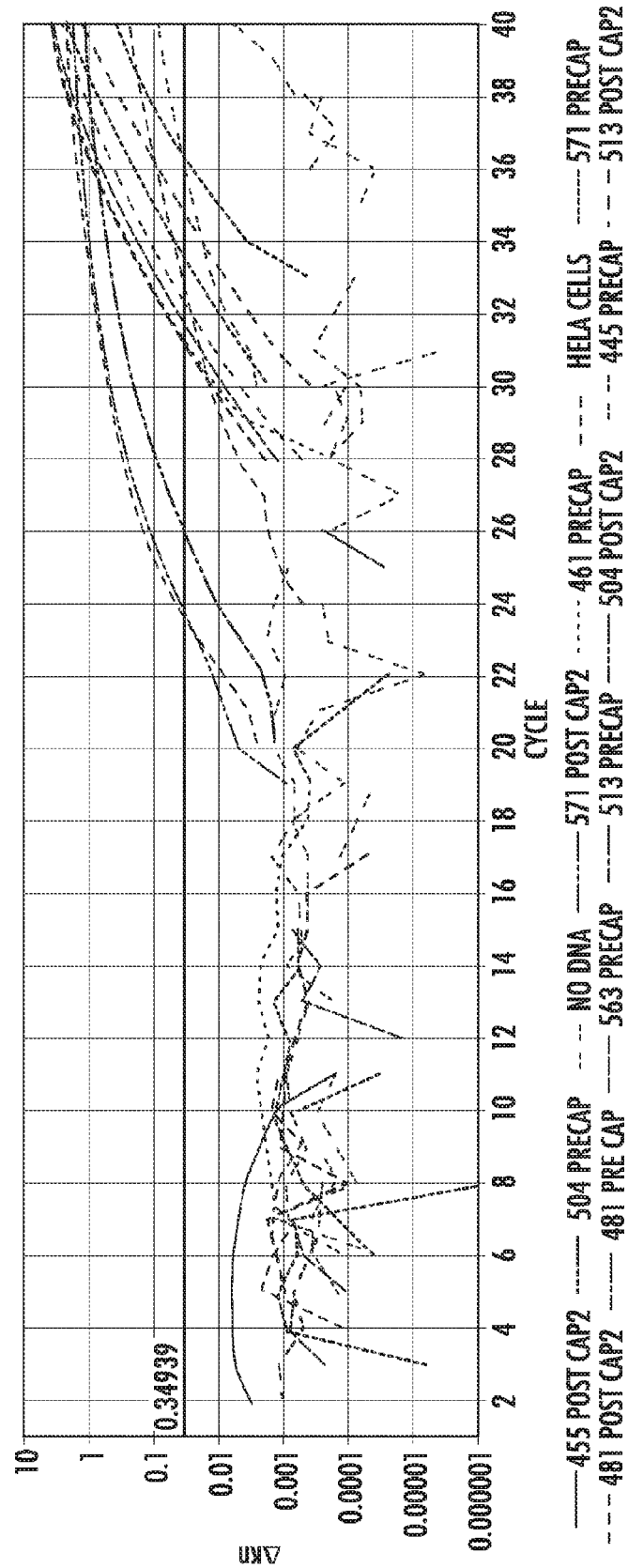
Figure 9A:
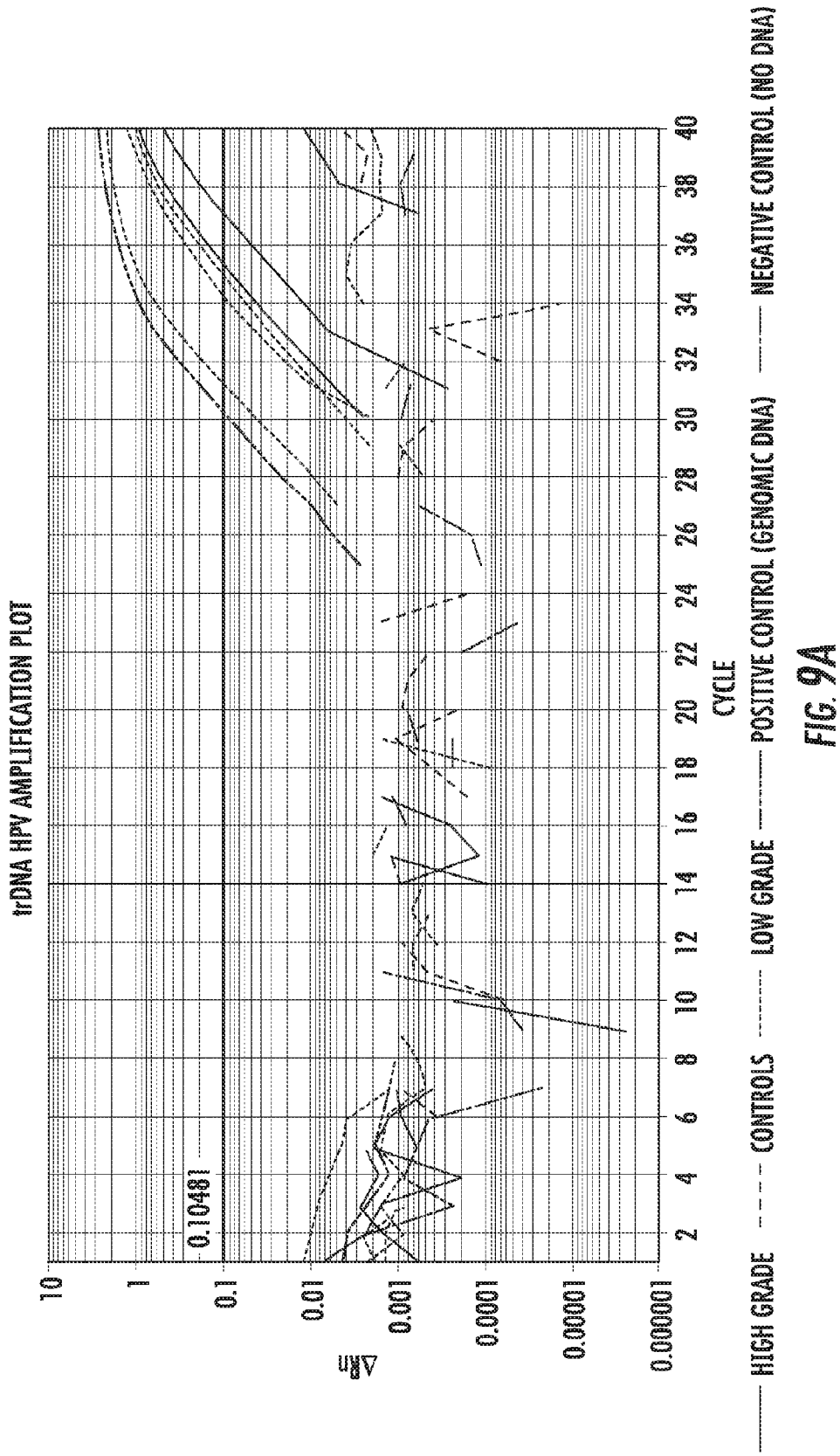
Figure 9B:
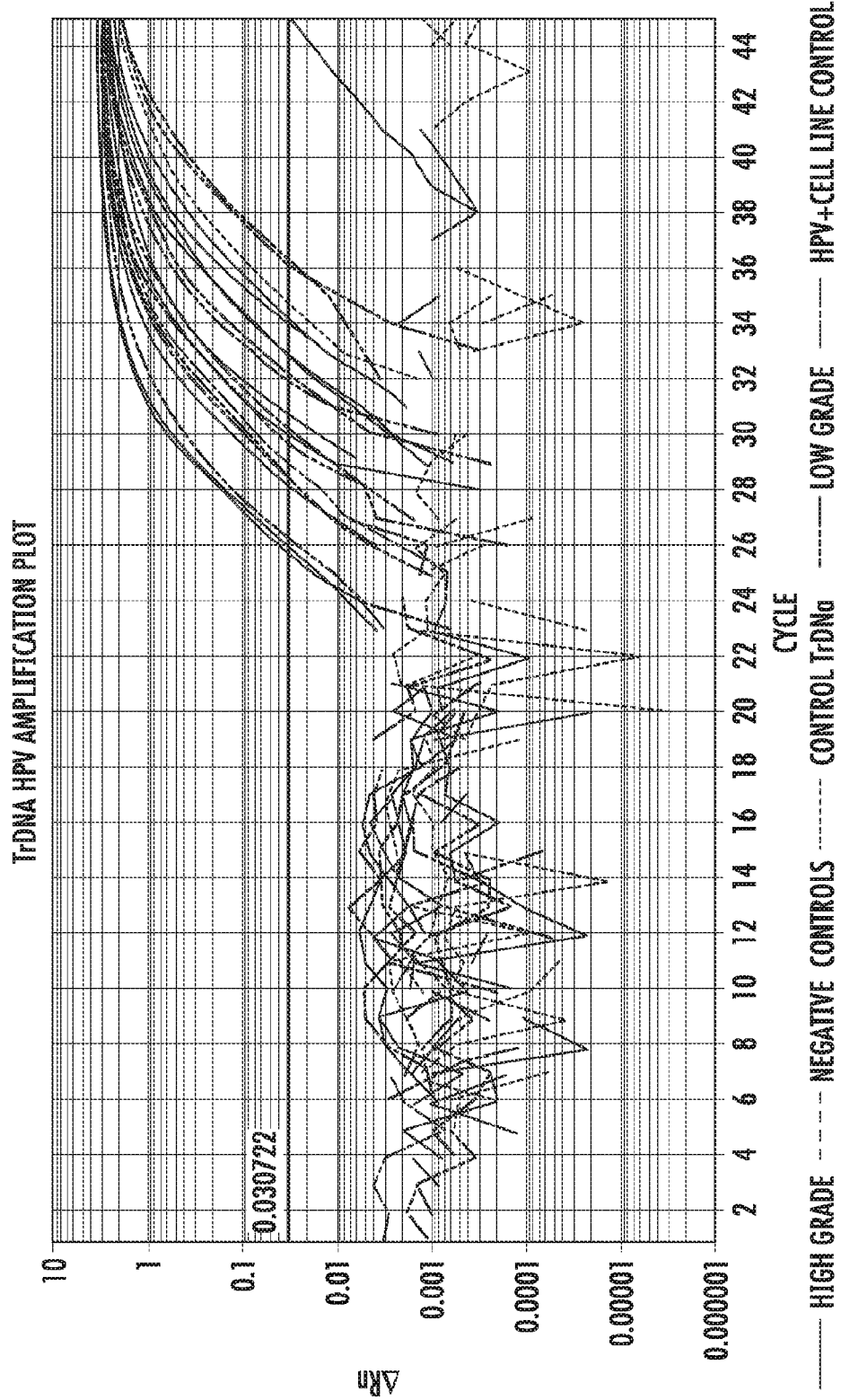
Figure 11A:
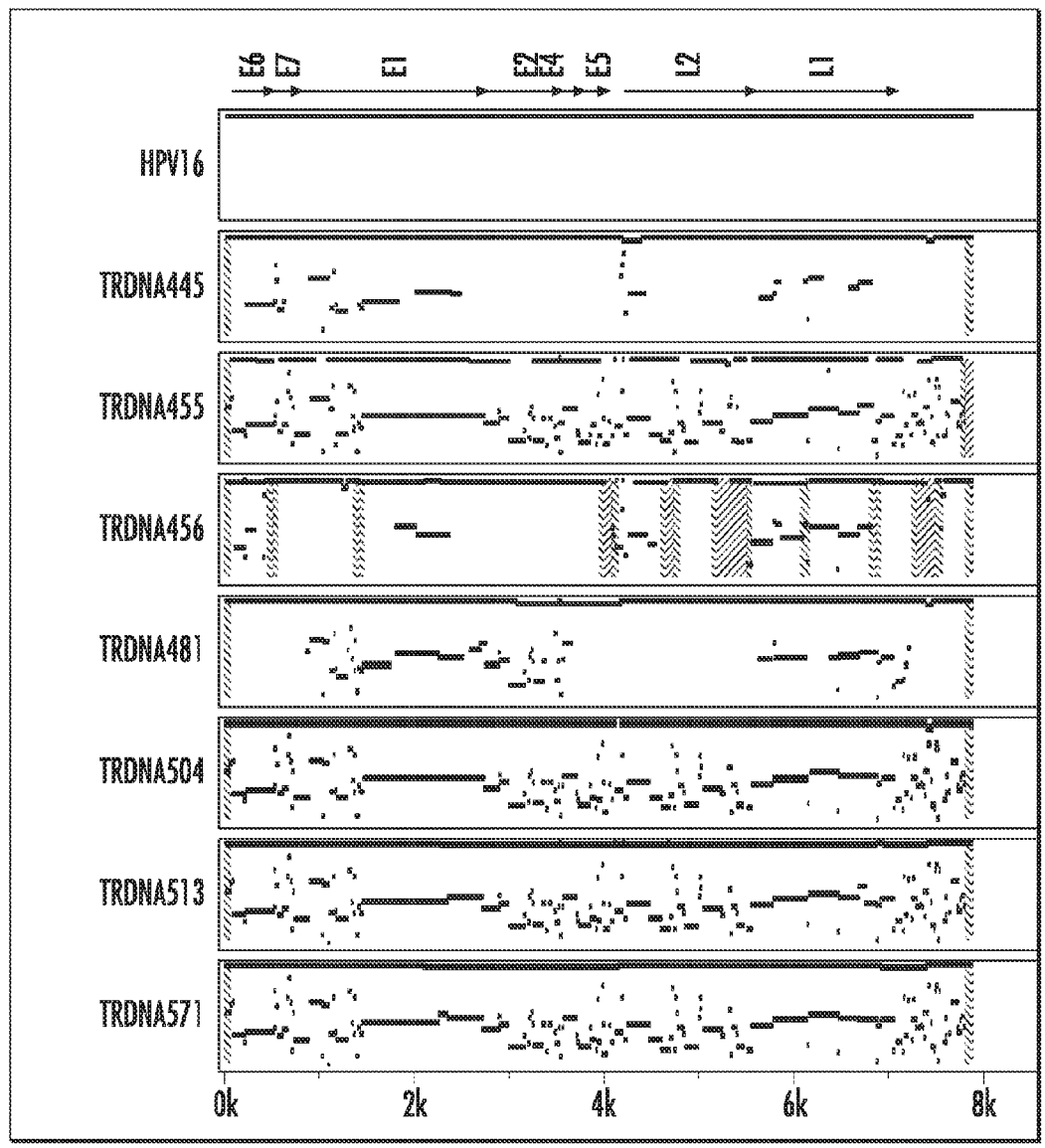
Figure 11B:
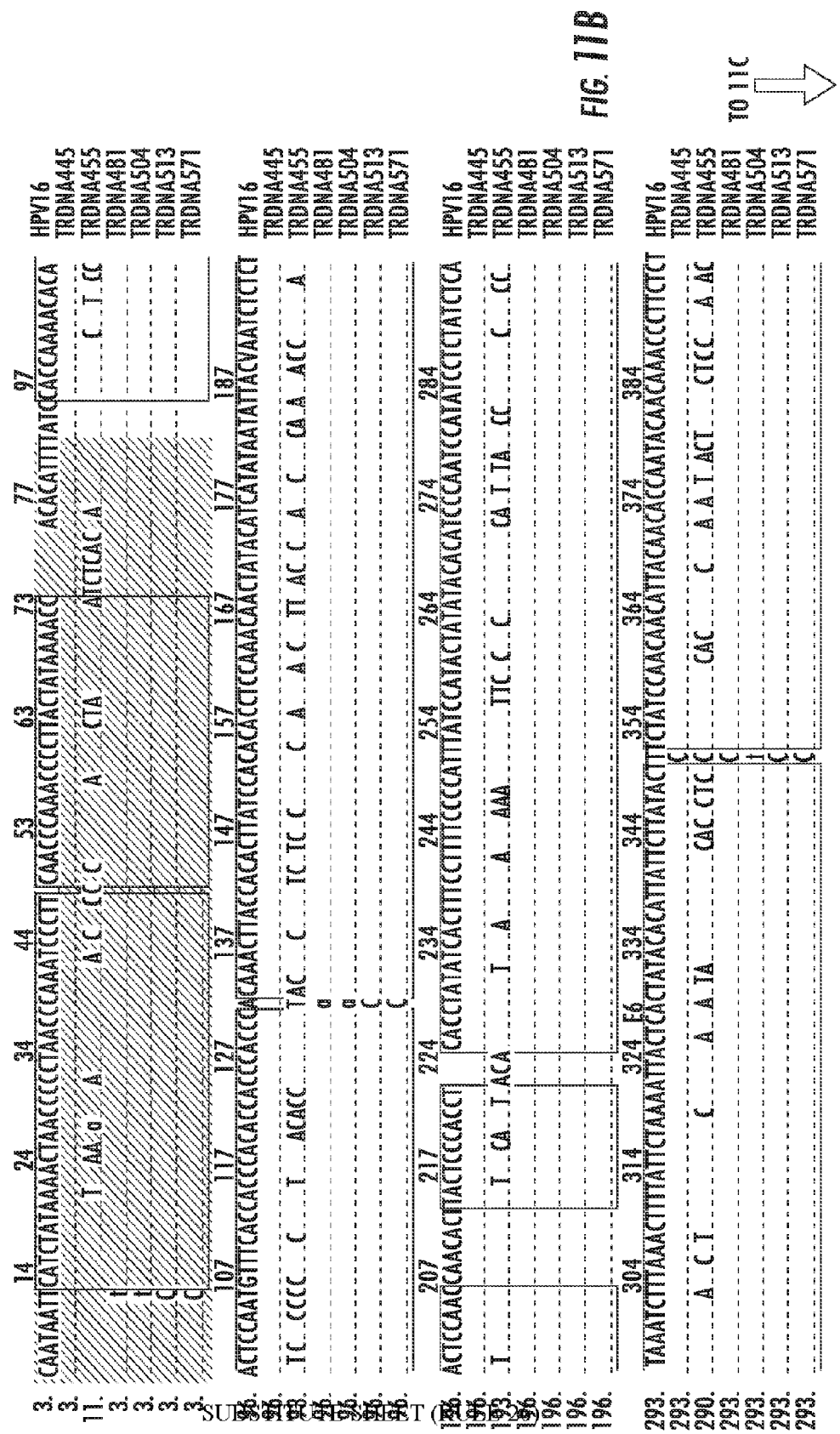
Figure 11C:
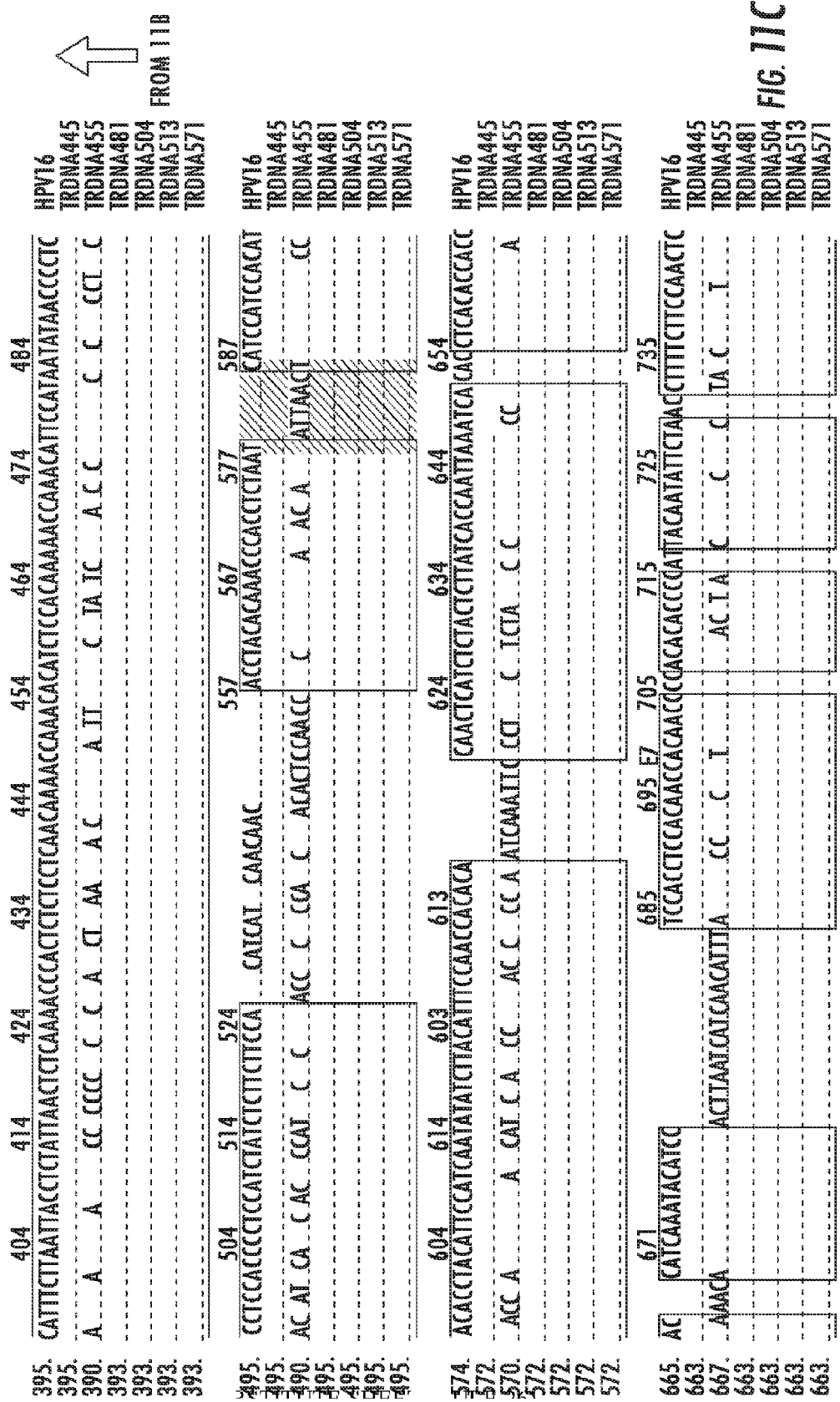

Having thus described the presently disclosed subject matter in general terms, reference will now be made to the accompanying Figures, which are not necessarily drawn to scale, and wherein:

FIGS. 1A and 1B show agarose gels (1.5%) of: (A) six low grade and six high grade TrDNA samples showing enrichment of small fragments; and (B) six low grade lesions (LGL), six high grade lesions (HGL), Caski (a cervical cancer cell line that has 600 copies of HPV) and SHIA (a cervical cancer cell line with only two HPV copies);

FIGS. 2A and 2B show: (A) HPV enriched DNA after first round of capture; and (B) HPV enriched DNA after second round of capture. The peak of interest is at the 1000 bp mark;

FIG. 3 shows the amplification plot of real time quantitative PCR utilizing SYBR green detection of an HPV-specific assay performed with the purified, HPV-enriched DNA from cervical cancer cell lines in comparison to pre-capture template and genomic control DNA;

FIGS. 4A and 4B show post-$2^{nd}$ capture LM-PCR DNA profiles assessed by high sensitivity DNA lab chip analysis on the BioAnalyzer 2100;

FIG. 5 shows the size profile of a short fragment template processed for sequencing on the GS Junior System. A library was prepared by ligation of bar-coded adaptors, and subsequently pooled with another bar-coded library, clonally amplified by emulsion PCR, and sequenced;

FIG. 6 shows a Read Length QC profile of pooled small fragments sequenced on the GS Junior System. The QC metrics for sequencing include Raw Wells number, Key Pass Wells number, Passed Filter Wells number, and Percent Pass Filter. Averages for these values from previous short fragment runs performed were 160,882 Raw Wells, 150,244 Key Pass Wells, 116,852 Passed Filter Wells and 78% Passed Filter wells. All exceeded manufacturer's specifications;

FIGS. 7A and 7B show: (A) amplification plots of real time quantitative PCR utilizing SYBR green detection of an HPVspecific assay (HPV TrDNA) performed with the purified, HPV-enriched DNA after sequence capture (Post-Capture) in comparison to pre-capture template (Pre-Capture) and genomic control DNA (HeLa Control); and (B) Pre- and Post-Capture qPCR comparison of sample 455 and CSCC7 cell line. Pre-(green) and Post-(red) capture qPCR results along with HeLa genomic DNA (blue) and No DNA controls (purple);

FIG. 8 shows Pre-(green) and Post-(red) capture HPV qPCR results for TrDNA samples 445, 481, 504, 513, and 571, together with HeLa genomic control (blue) and No DNA controls (purple). Pre-Capture LM-PCR for Tr-DNAs 461 and 563 also are included;

FIGS. 9A and 9B show amplification plots of real-time quantitative PCR utilizing SYBR green detection of an HPV-specific assay (HPV-TrDNA SYBR assay). Results shown are for TrDNA from women with low grade and high grade premalignant cervical lesions and normal cervical epithelium. DNA from HeLa, a cervical cancer cell line, was used as a genomic positive control. Ct ranges are variable in TrDNA samples, but are in a similar range as the genomic control. Most control TrDNA samples were negative for the assay;

FIG. 10 shows detailed multiple alignment analysis of TrDNA_445 CIN 2-3 and TrDNA_456 CIN 1; and FIG. 11A, FIG. 11B, and FIG. 11C show a large scale (8Kb) view (FIG. 11A) and close-up (1Kb) view (FIG. 11B and FIG. 11C) of multiple genome-wide pairwise alignments of four high risk HPV types (18, 31, 45, 52), five low risk HPV types (6, 11, 42, 53, 54), and seven HPV TrDNA samples against the HPV 16 reference genome. (CAATAAT-TCATCTATAAAACTAACCCCCTAACCCAAATCCCT-TCAACCCAAACCCCT TACTATAAAACC (SEQ ID NO:1); ACACATTTTATCCACCAAAACACAACTC-CAATGTTTCACCACCCACACCACCCACCC ACAAACTTACCACACTTATCCACACACCTC-CAAACAACTATACATCATATAATATTA CVAATCTCTCTACTCCAACCAACACTTACTC-CCACCT (SEQ ID NO:2); CACCTATATCACTTTC-CTTTTCCCCATTTATCCATACTATATACACATC-CCAATCCAT ATCCTCTATCTCATAAATCTTTAAACTTTTAT-TCTAAAATTACTCACTATACACATTA TTCT-TATACTTTCTATCCAACAACATTACAACACCAATA-CAACAAACCTTCTCTCAT TTCTTAATTACCTCTATTAACTCTCAAAAC-CCACTCTCTCCTCAACAAAACCAAACAC ATCTC-CACAAAAACCAAACATTCCATAATATAACCCCTC-CCTCCACCCCTCCATCTA TCTCTTCTTCCA (SEQ ID NO:3); ACCTACACAAACCCACCTCTAAT (SEQ ID NO:4); CATCCATCCACATACACCTACATTCCAT-CAATATATCTTACATTTCCAACCACACA (SEQ ID NO:5); CAACTCATCTCTACTCTTATCACCAATTAAAT-CACACCTCACACCACCAC (SEQ ID NO:6); CAT-CAAATACATCC (SEQ ID NO:7); TCCACCTCCACAAC-CACAACCCCACACACCCCATTACAATATTCTAAC-CTTTTCTTCC AACTC (SEQ ID NO:8); ACACTC-CAACC (SEQ ID NO:9); ACTTAATCATCAACATTTA (SEQ ID NO: 10)).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

HPV is a common sexually transmitted DNA virus comprised of more than 100 genotypes. Only 14 of the genotypes are considered pathogenic or high-risk (Kjaer et al., 2002). Multiple studies have linked genotypes 16, 18, 31, 33, 35, 39, 45, 51, 52, 56, 58, 59, 66, and 68 to disease progression (Monsonego, et al., 2004). Patients with a persistent infection with one of these types have an increased risk for developing severe dysplasia or cervical carcinoma (Cuschieri, 2004). The HPV viral genome is a double-stranded circular DNA approximately 7900 base pairs in length. The genome has eight overlapping open reading frames. There are six early (E) genes, two late (L) genes and one untranslated long control region. The L1 and L2 genes encode the major and minor capsid proteins. Early genes E6 and E7 regulate HPV viral replication. The E6 and E7 genes from the pathogenic genotypes are known oncogenes, which have been shown to directly contribute to malignant progression by promoting genomic instability (Doorbar, 2006). Clinical detection of HPV is typically performed by in vitro diagnostic assays that detect viral genomic DNA, specifically the L1 gene, on mucosa samples collected by cervical scraping.

Although infection with high-risk HPV is often transient, disappearing without consequences, studies have demonstrated that HPV screening tests are more cost-effective than the Pap smear or other morphological tests, as the infection precedes cellular transformation. Accurate tools to quantify the personalized dynamics of HPV high and low risk types in premalignant and cervical cancer lesions are lacking. A new generation of sequencing technologies is primed to provide sensitive and specific results to clinicians, investigators, and patients.

DNA methylation, the most important epigenetic modification known, is a chemical modification of the DNA molecule itself, which is carried out by an enzyme called DNA methyltransferase. DNA methylation can directly switch off gene expression by preventing transcription factors binding to promoters. However, a more general effect is the attraction of methyl-binding domain (MBD) proteins. These are associated with further enzymes called histone deacetylases (HDACs), which function to chemically modify histones and change chromatin structure. Chromatin containing acetylated histones is open and accessible to transcription factors, and the genes are potentially active. Histone deacetylation causes the condensation of chromatin, making it inaccessible to transcription factors and the genes are therefore silenced (Eberharter and Becker, 2002). The link between histone deacetylation and DNA methylation was the finding that MeCP2 physically interacts with the transcriptional co-repressor protein Sin3A, and in so doing recruits a histone de-acetylase (HDAC) to chromatin that contains methylated DNA (Tycko, 2000; Studnicki et al., 2005).

Experimental data suggest that genes involved in DNA methylation, histones modification and chromatin remodeling also become disrupted in cancer. Some of these will act as oncogenes, others as tumor-suppressor genes. Some will be altered by genetic lesions, others by epigenetic lesions (Esteller, 2006).

Approximately $10^{11-12}$ cells die each day as a byproduct of anabolism and catabolism, but also as a result of disease processes. The nucleic acids from each of these cells is broken (fragmented) into smaller pieces and disposed of in a variety of ways. Some of the DNA fragments are carried away by the blood stream that perfuses every tissue and organ of the body. It is estimated that more than one gram of a complex mix of human and non-human DNA circulates in the blood stream of a person daily. A very small portion of this circulating DNA crosses the kidney barrier and can be found in the urine as Transrenal DNA (TrDNA) in a form of 150-200 bp fragments. TrDNA molecules are relatively short, fragmented pieces of circulating DNA that get filtered by the kidneys and can be isolated from urine. Transrenal tumor DNA has been reported in urine from patients with cancer and tuberculosis. Fetal TrDNA has been detected in maternal urine.

The kidney acts as a filter and presents purified TrDNA in the urine and, therefore, simplifies the sample preparation and DNA isolation steps currently required in the laboratory by other testing methods. As such, this approach permits frequent sampling and the sampling of large populations. Moreover, urine sampling, unlike cervical mucosa sampling, is a method that is preferred and better accepted culturally. Urine samples are acceptable in clinical practice and are used to screen for chlamydia and gonorrhea. HPV TrDNA detection in urine does not interfere with the natural history of the infection, whereas scraping cells from the cervix, vagina, or glands may create microlesions or induce an inflammatory reaction.

Further, the urine collection procedure is non-invasive, does not require the involvement of trained medical staff, and facilitates repeated testing with minimal discomfort for the patient. TrDNA is also stable at room temperature for extended periods. The presently disclosed urine-based TrDNA HPV assays provide comparable performance to available commercial cervical cell-based high-risk HPV assays and offer a significant advantage for the identification of HPV in males and where vaginal swab sample collection presents a logistic or privacy concern.

Accordingly, the presently disclosed subject matter provides methods for detecting HPV Trans-Renal DNA (TrDNA) from urine. In some embodiments, the methods comprise using a sequence-based method to detect high-risk HPV-TrDNA. The term "sequence-based method" as used herein means that the method relies on sequencing of nucleic acids to help detect HPV TrDNA or to determine if a subject has or is at risk for developing cancer.

I. Methods for Detecting HPV Trans-Renal DNA from Urine

Accordingly, in some embodiments, the presently disclosed subject matter provides a sequence-based method for detecting HPV Trans-Renal DNA (TrDNA) in a subject, the method comprising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises: (i) preparing a library of the low molecular weight, fragmented cell-free nucleic acids; (ii) amplifying the library using PCR to form a pre-capture PCR library; (iii) hybridizing the pre-capture PCR library to a custom-designed pool of HPV-specific capture probes to form a post-capture PCR library; (iv) amplifying the post-capture PCR library to produce one or more enriched HPV TrDNA; and (v) optionally repeating steps (iii) and (iv); (d) adding at least one index to the one or more enriched HPV TrDNA; (e) performing multiplexed sequencing of the one or more enriched HPV TrDNA having at least one index added thereto to produce a multiplexed nucleotide sequence; (f) performing a sequence alignment between the multiplexed nucleotide sequence and the nucleotide sequence of one or more known HPV genotypes; and (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject.

The urine sample is preferably freshly delivered from a subject. However the presently disclosed methods are applicable to urine samples that have been stored. For example, a urine sample may be stored in the refrigerator or freezer for an extended period of time, such as an hour, a day, a week, or a month. If the urine sample is stored in the freezer, it may be stored for longer than a month.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

Nucleic acid molecules referred to herein as "cell-free" are nucleic acid molecules found outside the cell. For example, circulating DNA can be found in the blood or urine of a subject. The term "fragmented" as used herein refers to molecules that have been broken apart into separate parts from whole molecule. The term "isolated" designates a biological material, such as a nucleic acid, that has been removed from its original environment (the environment in which it is naturally present). For example, isolating a cell-free nucleic acid from urine means to separate the nucleic acid from other molecules found in urine, such as lipids, carbohydrates and proteins. Isolating or purifying the cell-free nucleic acids may occur by any technique known in the art, for example, extraction with organic solvents, filtration, precipitation, absorption on solid matrices (e.g., silica resin, hydroxyapatite or ion exchange), affinity chromatography (e.g., via sequence specific capture or nucleic acid specific ligands), molecular exclusion chromatography, and the like. However, the purification method must be appropriate for the isolation of DNA (single- or double-strand) whose dimensions are smaller than 1000 nucleotide pairs. Even more preferably, the purification is specific for fragments that are smaller than 500 nucleotides, and even more preferably, fragments whose length are less than 300 or 250 base pairs. A nucleic acid is substantially pure or isolated when a sample contains at least about 50%, preferably 60 to 75%, of nucleic acid. In some embodiments, isolating cell-free nucleic acids from the urine sample occurs by using Q-Sepharose and/or silica resin.

The term "detect" as used herein means to discover the existence of a molecule, such as DNA or RNA. For example, in some embodiments, the presently disclosed methods help detect the presence of HPV TrDNA. In other embodiments, the presently disclosed methods help detect the presence of HPV TrRNA.

In some embodiments, a high-risk HPV-specific, solution-based capture method is used to enrich the low molecular weight, fragmented cell-free nucleic acids after isolation of the nucleic acids from the urine sample. In this solution-based capture method, a DNA sequencing library is prepared with the cell-free nucleic acids and the library is amplified. In some embodiments, ligation-mediated PCR (LM-PCR) is used to amplify the library using PCR to form a pre-capture PCR library. In this method, in some embodiments, small DNA linkers are ligated to the DNA of interest and multiple primers are annealed to the DNA linkers. The term "pre-capture" as used herein refers to the steps before enrichment of the low molecular weight, fragmented cell-free nucleic acids.

In some embodiments, enrichment of the low molecular weight, fragmented cell-free nucleic acids occurs by using a high-risk HPV-specific, solution-based capture method. The term "enriching" as used herein means to purify or partially purify the molecule of interest. For example, enriching for HPV TrDNA in a sample means to use a method or means to have more HPV TrDNA molecules in the sample and less of other molecules. The term "solution-based" as used herein refers to a method that is performed in solution. This method preferably occurs in a single tube, although multiple tubes may be used if desired. The term "tube" as used herein refers to common tubes used in a laboratory setting usually for research experiments. They are usually made of glass or some sort of plastic, such as Eppendorf tubes, and they hold small quantities of substances undergoing experimentation or testing. By "small quantities", it is meant less than 10 milliliters, such two milliliters or less.

In general, in sequence capture (solution-based capture) methods, a DNA sequencing library is prepared from the DNA of interest, the library is amplified by PCR, the library is hybridized to a custom-designed pool of sequence capture probes, and amplified using PCR, and then the amplification products (found in the post-capture library) are assessed by sequencing, PCR, and the like. In a double capture or dual capture method, the post-capture library is hybridized again to the custom-designed pool of sequence capture probes and amplified again before being assessed. These methods allow the DNA of interest, such as the low molecular weight, fragmented cell-free nucleic acids described herein, to be "captured" by the custom-designed pool of sequence capture probes. Examples of commercial methods that employ solution-based capture methods include the custom-made Roche SeqCap EZ library method (Roche NimbleGen, Madison, Wis.) and the Agilent Next Generation Sequencing Solutions (Agilent Technologies, Santa Clara, Calif.).

In some embodiments, in these methods, enrichment specificity is defined as the fraction of nucleic acid fragments obtained at the end of an experiment that were explicitly targeted for capture at the beginning. This is often measured as the percentage of sequence reads, or sequenced bases, from an experiment that align with the targeted portion of a reference sequence. Along with sequence coverage uniformity across the target, enrichment specificity is a major determinant of overall process efficiency. In solution-based capture methods, specificity can be determined by several factors, including probe design, hybridization and washing conditions, and repetitive element and library adapter blocking strategies.

In some embodiments, the presently disclosed methods disclose a method using solution-based capture to capture or detect high-risk HPV TrDNA from urine. In other embodiments, the methods are performed with only one round of hybridization and amplification. In still other embodiments, a dual sequence-capture method is performed comprising two rounds of hybridization and amplification of the library.

In some embodiments, the custom-designed pool of HPV-specific capture probes is designed to capture most or all of the genomes of high-risk HPV-specific types. In other embodiments, the custom-designed pool of HPV-specific capture probes is designed to capture only some regions of the genotype-specific regions of at least one high-risk HPV genome, such as 1, 2, 3, 4, or 5 or more regions. In still other embodiments, the custom-designed pool of HPV-specific capture probes is designed to capture 2 to 3 regions of the HPV genome that distinguishes high-risk from low-risk HPV types. In further embodiments, the custom-designed pool of HPV-specific capture probes does not capture low-risk HPV types.

In some embodiments, enrichment of the low molecular weight, fragmented cell-free nucleic acids occurs by using a dual solution-based capture method in which the first round of capture uses a set of the custom-designed pool of HPV-specific capture probes designed to capture most or all of the genome of some high-risk HPV types and the second round of capture uses another set of custom-designed pool of HPV-specific capture probes designed to capture only some of the regions of the HPV genome that distinguish high-risk from low-risk HPV types, such as 2 to 3 regions. In another embodiment, both rounds of capture use a set of the custom-designed pool of HPV-specific capture probes designed to capture most or all of the genome of some high-risk HPV types. In still another embodiment, both rounds of capture use a set of the custom-designed pool of HPV-specific capture probes designed to capture only some of the regions of the HPV genome that distinguish high-risk from low-risk HPV types, such as 2 to 3 regions. In preferred embodiment, the capture probes only capture high-risk HPV genotypes and do not capture low-risk HPV genotypes. Cancer lines that comprise low or high copies of a high-risk HPV type, such as HPV16, can be used as a positive control to determine if the custom-designed pool of HPV-specific capture probes is designed correctly.

The term "multiplexed sequencing" as used herein refers to high-throughput sequencing in which samples are uniquely tagged with short identifying sequences known as indexes or barcodes, pooled, and then sequenced together in a single lane. Th resulting combined sequence data are subsequently sorted by the indexes before analysis. The method of adding indexes to DNA and multiplexed sequencing are well known in the art.

In some embodiments, the method further comprises performing quantitative PCR (qPCR) to amplify the one or more enriched HPV TrDNA. In other embodiments, amplifying the one or more enriched HPV TrDNA amplifies the E1 region of at least one HPV genotype. In further embodiments, amplifying the one or more enriched HPV TrDNA amplifies most or all of the genotype-specific regions of at least one HPV genome.

In some embodiments, the one or more known HPV genotypes are one or more known high-risk HPV genotypes. In other embodiments, the one or more known high-risk HPV genotypes are from one or more HPV genotypes selected from the group consisting of HPV16, HPV18, HPV31, HPV33, HPV35, HPV39, HPV45, HPV51, HPV52, HPV56, HPV58, HPV59, and HPV68. In still other embodiments, the presence of the one or more known high-risk HPV genotypes is indicative that the subject has or is at risk for developing a cancer. In further embodiments, the cancer is selected from the group consisting of cervical, anal, penile, and oropharyngeal.

In some embodiments, the subject is human. In other embodiments, the method further comprises detecting human TrDNA by using the presently disclosed methods. In still other embodiments, the custom-designed pool of HPV-specific capture probes also comprises probes that are capable of capturing human TrDNA.

The term "high-risk HPV" as used herein refers to those HPV types or strains that may progress to precancerous lesions and invasive cancer. For example, high-risk HPV strains that are known or thought to cause cervical cancer include HPV 16, 18, 26, 31, 33, 35, 39, 45, 51, 52, 53, 56, 58, 59, 66, 68, 73, and 82. High-risk HPV strains that are known or thought to cause anal lesions include HPV 6, 16, 18, 31, 53, and 58. In some embodiments, the high-risk HPV TrDNA is selected from the group consisting of HPV16, HPV18, HPV31, HPV33, HPV35, HPV39, HPV45, HPV51, HPV52, HPV56, HPV58, HPV59 and HPV68.

In general, PCR refers to an in vitro method for amplifying or replicating a specific polynucleotide template sequence. The PCR reaction involves a repetitive series of temperature cycles. The reaction mix usually comprises dNTPs (each of the four deoxynucleotides dATP, dCTP, dGTP, and dTTP), primers, buffers, DNA polymerase, and target nucleic acid molecule or template. The PCR step can use a variety of thermostable DNA-dependent DNA polymerases, such as Taq DNA polymerase, which has a 5'-3' nuclease activity but lacks a 3'-5' proofreading endonuclease activity. In real-time or quantitative PCR, the DNA is amplified and simultaneously quantified. Variations on the general PCR method are known in the art.

The term "multiplexed sequencing" as used herein refers to high-throughput sequencing in which samples are uniquely tagged with short identifying sequences known as indexes or barcodes, pooled, and then sequenced together in a single lane. Th resulting combined sequence data are subsequently sorted by the indexes before analysis. The method of adding indexes to DNA and multiplexed sequencing are well known in the art.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences that differ by such conservative substitutions are said to have sequence similarity. Approaches for making this adjustment are well-known to those of skill in the art.

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least about 60% or more identity, such as 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or higher identity compared to a reference sequence using one of the alignment programs described using standard parameters.

II. Methods for Detecting Methylated HPV Trans-Renal DNA and Methylated Human Trans-Renal DNA from Urine In some embodiments, the presently disclosed subject matter provides a sequence-based method for detecting methylated HPV Trans-Renal DNA (TrDNA) in a subject, the method comprising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises: (i) preparing a library of the low molecular weight, fragmented cell-free nucleic acids; (ii) amplifying the library using PCR to form a pre-capture PCR library; (iii) hybridizing the pre-capture PCR library to a custom-designed pool of HPV-specific capture probes to form a post-capture PCR library; (iv) amplifying the post-capture PCR library to produce one or more enriched HPV TrDNA; and (v) optionally repeating steps (iii) and (iv); (d) adding at least one index to the one or more enriched HPV TrDNA; (e) performing multiplexed sequencing of the one or more enriched HPV TrDNA having at least one index added thereto to produce a multiplexed nucleotide sequence; (f) performing a sequence alignment between the multiplexed nucleotide sequence and the nucleotide sequence of one or more known HPV genotypes; and (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject; wherein prior to step (d) the post-capture library is treated with a bisulfite compound and is amplified using PCR to form one or more amplified methylated HPV TrDNA; and further wherein at least a 70% sequence identity between the multiplexed nucleotide sequence and the nucleotide sequence of the one or more known methylated HPV genotypes means that methylated HPV TrDNA has been detected in the subject.

In some embodiments, the low molecular weight, fragmented cell-free nucleic acids are from about 150 to about 250 base pairs. In other embodiments, isolating the one or more low molecular weight, fragmented cell-free nucleic acids from the urine sample occurs by using Q-Sepharose and/or silica resin.

In some embodiments, ligation-mediated PCR (LM-PCR) is used to amplify the library using PCR to form a pre-capture PCR library. In other embodiments, the method further comprises performing quantitative PCR (qPCR) to amplify the one or more amplified methylated HPV TrDNA. In still other embodiments, amplifying the one or more amplified methylated HPV TrDNA amplifies the E1 region of at least one HPV genotype. In further embodiments, amplifying the one or more amplified methylated HPV TrDNA amplifies most or all of the genotype-specific regions of at least one HPV genome.

In some embodiments, the one or more known methylated HPV genotypes are one or more known high-risk methylated HPV genotypes. In other embodiments, the one or more known high-risk methylated HPV genotypes are from one or more methylated HPV genotypes selected from the group consisting of HPV16, HPV18, HPV31, HPV33, HPV35, HPV39, HPV45, HPV51, HPV52, HPV56, HPV58, HPV59, and HPV68. In still other embodiments, the presence of the one or more known high-risk methylated HPV genotypes is indicative that the subject has or is at risk for developing a cancer. In further embodiments, the cancer is selected from the group consisting of cervical, anal, penile, and oropharyngeal.

DNA methylation is a biochemical process whereby a methyl group is added to the cytosine or adenine DNA nucleotides. Bisulfite compounds, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligo- nucleotide that selectively hybridizes to a nucleotide sequence of the target gene that either contains uracil residues or that lacks uracil residues, but not both, and detecting selective hybridization (or the absence thereof) of the oligonucleotide.

In some embodiments, the subject is human. In other embodiments, the custom-designed pool of HPV-specific capture probes further comprises probes to capture human TrDNA.

In some embodiments, the presently disclosed methods provide a sequencing based method to identify high risk HPV which is complemented by two additional sequencing based assays: methylated HPV TrDNA and methylated Human TrDNA. The two additional TrDNA assays, com- bined with the HPV TrDNA assay provide progression information, for those patients that have already been found to have high-risk HPV, thus enabling risk stratification and personalized clinical management.

In some embodiments, the presently disclosed subject matter provides a sequence-based method for detecting methylated human Trans-Renal DNA (TrDNA) in a subject, the method comprising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for human TrDNA using a high-risk human-specific solution- based capture method to enrich the human genome to produce one or more enriched human TrDNA, wherein enriching the one or more low molecular weight fragmented cell-free nucleic acids comprises: (i) preparing a library of the low molecular weight, fragmented cell-free nucleic acids; (ii) amplifying the library using PCR to form a pre-capture PCR library; (iii) hybridizing the pre-capture PCR library to a custom-designed pool of human-specific capture probes to form a post-capture PCR library; (iv) amplifying the post-capture PCR library to produce one or more enriched human TrDNA; and (v) optionally repeating steps (iii) and (iv); (d) adding at least one index to the one or more enriched human TrDNA; (e) performing multi- plexed sequencing of the one or more enriched human TrDNA having at least one index added thereto to produce a multiplexed nucleotide sequence; (f) performing a sequence alignment between the multiplexed nucleotide sequence and the nucleotide sequence of the human genome; and (g) determining the percentage sequence identity between the multiplexed nucleotide sequence and the nucleotide sequence of the human genome; wherein prior to step (d) the post-capture library is treated with a bisulfate compound and is amplified using PCR to form one or more amplified methylated human TrDNA; and further wherein at least a 60% sequence identity between the multiplexed nucleotide sequence and the nucleotide sequence of the human genome means that methylated human TrDNA has been detected in the subject.

III. Methods for Predicting or Screening for Cancer by Detecting HPV Trans-Renal DNA from Urine The presently disclosed subject matter also provides methods for predicting or screening for cancer in a subject. More particularly, in some embodiments, the presently dis- closed subject matter provides a sequence-based method for predicting or screening for cancer by detecting HPV Trans- Renal DNA (TrDNA) in a subject, the method comprising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids com- prises: (i) preparing a library of the low molecular weight, fragmented cell-free nucleic acids; (ii) amplifying the library using PCR to form a pre-capture PCR library; (iii) hybrid- izing the pre-capture PCR library to a custom-designed pool of HPV-specific capture probes to form a post-capture PCR library; (iv) amplifying the post-capture PCR library to produce one or more enriched HPV TrDNA; and (v) option- ally repeating steps (iii) and (iv); (d) adding at least one index to the one or more enriched HPV TrDNA; (e) per- forming multiplexed sequencing of the one or more enriched HPV TrDNA having at least one index added thereto to produce a multiplexed nucleotide sequence; (f) performing a sequence alignment between the multiplexed nucleotide sequence and the nucleotide sequence of one or more known HPV genotypes; and (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject; wherein at least a 60% sequence identity between the multiplexed nucleotide sequence and the nucleotide sequence of the one or more known high-risk HPV geno- types is indicative that the subject has or is at risk for developing a cancer.

In some embodiments, the presently disclosed subject matter provides a sequence-based method for predicting or screening for cancer by detecting high-risk methylated HPV Trans-Renal DNA (TrDNA) in a subject, the method com- prising: (a) providing a urine sample from the subject; (b) isolating one or more low molecular weight, fragmented cell-free nucleic acids from the urine sample; (c) enriching the one or more low molecular weight fragmented cell-free nucleic acids isolated from the urine sample for HPV TrDNA using a high-risk HPV-specific solution-based cap- ture method to enrich the HPV genome to produce one or more enriched HPV TrDNA, wherein enriching the one or more low molecular weight fragmented cell-free nucleic acids comprises: (i) preparing a library of the low molecular weight, fragmented cell-free nucleic acids; (ii) amplifying the library using PCR to form a pre-capture PCR library; (iii) hybridizing the pre-capture PCR library to a custom-de- signed pool of HPV-specific capture probes to form a post-capture PCR library; (iv) amplifying the post-capture PCR library to produce one or more enriched HPV TrDNA; and (v) optionally repeating steps (iii) and (iv); (d) adding at least one index to the one or more enriched HPV TrDNA; (e) performing multiplexed sequencing of the one or more enriched HPV TrDNA having at least one index added thereto to produce a multiplexed nucleotide sequence; (f) performing a sequence alignment between the multiplexed nucleotide sequence and the nucleotide sequence of one or more known HPV genotypes; and (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject; wherein prior to step (d) the post-capture library is treated with a bisulfite compound and is amplified using PCR to form one or more amplified methylated HPV TrDNA; and further wherein at least a 70% sequence identity between the multiplexed nucleotide sequence and the nucleotide sequence of the one or more known high-risk methylated HPV genotypes is indicative that the subject has or is at risk for developing a cancer.

In some embodiments, the presently disclosed subject matter provides a method for predicting or screening for cancer by detecting methylated HPV Trans-Renal DNA (TrDNA) in a subject, the method comprising steps (a)-(g) provided hereinabove, wherein prior to step (c.iii) the pre-capture PCR library is hybridized to a custom-designed pool of Human-specific capture probes that comprise Differentially Methylated Regions (DMRs) in the human genome to form a post-capture PCR library of Human TrDNA; (iv) amplifying the post-capture PCR library to produce one or more enriched Human TrDNA; and (v) optionally repeating steps (iii) and (iv); and (vi) the post-capture library is treated with a bisulfite compound and is amplified using PCR to form one or more amplified methylated Human TrDNA; and further (d) adding at least one index to the one or more enriched Human TrDNA; (e) performing multiplexed sequencing of the one or more enriched Human TrDNA having at least one index added thereto to produce a multiplexed nucleotide sequence; (f) performing a sequence alignment between the multiplexed nucleotide sequence and the nucleotide sequence of the human genome; and (g) determining the percentage sequence identity between the multiplexed nucleotide sequence and the nucleotide sequence of the one or DMRs in the human genome; wherein at least a 60% sequence identity between the multiplexed nucleotide sequence and the nucleotide sequence of the one or more known Human TrDNA reads means that methylated Human TrDNA has been detected in the subject.

In some embodiments, the low molecular weight, fragmented cell-free nucleic acids are from about 150 to about 250 base pairs. In other embodiments, isolating the one or more low molecular weight, fragmented cell-free nucleic acids from the urine sample occurs by using Q-Sepharose and/or silica resin.

In some embodiments, the one or more known high-risk HPV genotypes are from one or more HPV genotypes selected from the group consisting of HPV16, HPV18, HPV31, HPV33, HPV35, HPV39, HPV45, HPV51, HPV52, HPV56, HPV58, HPV59, and HPV68. In other embodiments, the cancer is selected from the group consisting of cervical, anal, penile, and oropharyngeal.

In some embodiments, the subject is human. In other embodiments, the custom-designed pool of HPV-specific capture probes further comprises probes to capture human TrDNA. In still other embodiments, the method further comprises detecting human methylated TrDNA.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. In particular embodiments, the cancer is selected from the group consisting of cervical, anal, penile, and oropharyngeal cancers.

The subject referred to in the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods

Cell-free nucleic acids from urine samples (10 mL) of 41 women with 23 LGL (low-grade) and 18 HGL (high-grade) cervical lesions and 31 women with normal cytology were adsorbed on a Q-Sepharose resin followed by a silica-based DNA extraction (Melkonyan, et al., 2008). A custom-designed pool of HPV-specific dual sequence capture probes was used for library amplification and target selection (SeqCap EZ Choice Library, Roche NimbleGen, Madison, Wis.). A pre-capture amplification of the library was performed with ligation-mediated PCR (LM-PCR) using primers complementary to the adaptors, followed by two rounds of hybridization to the HPV-specific SeqCap EZ Choice Library. Amplified captured DNA from HPV infected cell lines, HeLa (hpv18) CSCC7 (hpv16), and HPV TrDNA samples from premalignant cervical lesions were processed for multiplexed sequencing on the GS Junior System (Roche, Basel, CH). Following completion of the pyrosequencing run, signal processing was performed, followed by detailed analyses.

An hpvE1 region common to thirteen high-risk HPV types for cervical cancer (HPV16, 18, 31, 33, 35, 39, 45, 51, 52, 56, 58, 59 and 68) was amplified for the SYBR green qPCR assay. Known GenBank Accession Numbers for high- and low-risk HPV types are shown in Table 1. Some target sequences of high-risk HPV types that can be used in the presently disclosed methods are shown in Table 2. A single primer pair differentiated high-risk HPV types from low-risk counterparts. The high-risk type specific marker is inside the E1 gene of HPV genome. The copy number of the HPV derived biomarker was at least 2000 copies/mL of urine. At least one of the advantages of using a urine specimen was that approximately 20,000 copies of the target DNA could be made available from 10 mL of urine. DNA was amplified by PCR using a FAM-labeled forward primer and an unlabeled reverse primer. These primers generated a 93-96 bp amplicon.

TABLE 1

GenBank Accession Numbers of HPV types.

| HIGH RISK | | LOW RISK | |
| --- | --- | --- | --- |
| HPV Type | GenBank Accession No. | HPV Type | GenBank Accession No. |
| 16 | NC_001526 | 6 | FR751336 |
| 18 | AY262282 | 11 | EU918768 |
| 31 | HQ537687 | 42 | GQ472847 |
| 33 | HQ537707 | 44 | HPU31788 |
| 35 | HQ537729 | 53 | GQ472849 |
| 39 | M62849 | 54 | NC_001676 |
| 45 | EF202166 | 61 | HPU31793 |
| 52 | HQ537751 | 72 | X94164 |
| 56 | EF177180 | 81 | AJ620209 |
| 58 | HQ537777 | | |
| 59 | X77858 | | |
| 68b | FR751039 | | |

TABLE 2

Target sequences of high-risk HPV types.

| HPV Type | GenBank Accession No. | Capture Target Start | Capture Target End |
| --- | --- | --- | --- |
| 18 | AY262282_1 | 9 | 1090 |
| 18 | AY262282_1 | 1091 | 2371 |
| 18 | AY262282_1 | 2375 | 2720 |
| 18 | AY262282_1 | 2825 | 3422 |
| 18 | AY262282_1 | 3432 | 3948 |
| 18 | AY262282_1 | 3951 | 4220 |
| 18 | AY262282_1 | 4226 | 5617 |
| 18 | AY262282_1 | 5618 | 6286 |
| 18 | AY262282_1 | 6295 | 7122 |
| 18 | AY262282_1 | 7151 | 7435 |
| 18 | AY262282_1 | 7446 | 7830 |
| 56 | EF177180_1 | 3 | 7814 |
| 45 | EF202166_1 | 5 | 1307 |
| 45 | EF202166_1 | 1308 | 1878 |
| 45 | EF202166_1 | 1885 | 2329 |
| 45 | EF202166_1 | 2333 | 2690 |
| 45 | EF202166_1 | 2783 | 3373 |
| 45 | EF202166_1 | 3386 | 4176 |
| 45 | EF202166_1 | 4211 | 5598 |
| 45 | EF202166_1 | 5613 | 7802 |
| 68b | FR751039_1 | 11 | 2625 |
| 68b | FR751039_1 | 2693 | 2879 |
| 68b | FR751039_1 | 2889 | 3935 |
| 68b | FR751039_1 | 4016 | 4849 |
| 68b | FR751039_1 | 4867 | 7108 |
| 68b | FR751039_1 | 7116 | 7780 |
| 31 | HQ537687_1 | 11 | 2645 |
| 31 | HQ537687_1 | 2721 | 4122 |
| 31 | HQ537687_1 | 4131 | 6505 |
| 31 | HQ537687_1 | 6506 | 7850 |
| 33 | HQ537707_1 | 5 | 1250 |
| 33 | HQ537707_1 | 1264 | 2156 |
| 33 | HQ537707_1 | 2178 | 2674 |
| 33 | HQ537707_1 | 2776 | 3243 |
| 33 | HQ537707_1 | 3251 | 3969 |
| 33 | HQ537707_1 | 3996 | 4069 |
| 33 | HQ537707_1 | 4087 | 4159 |

TABLE 2-continued

Target sequences of high-risk HPV types.

| | | | |
|---|---|---|---|
| 33 | HQ537707_1 | 4166 | 5574 |
| 33 | HQ537707_1 | 5611 | 6243 |
| 33 | HQ537707_1 | 6258 | 6569 |
| 33 | HQ537707_1 | 6571 | 7796 |
| 35 | HQ537729_1 | 13 | 2653 |
| 35 | HQ537729_1 | 2680 | 4156 |
| 35 | HQ537729_1 | 4161 | 7882 |
| 52 | HQ537751_1 | 9 | 2222 |
| 52 | HQ537751_1 | 2240 | 2697 |
| 52 | HQ537751_1 | 2710 | 3833 |
| 52 | HQ537751_1 | 3871 | 5623 |
| 52 | HQ537751_1 | 5670 | 7887 |
| 58 | HQ537777_1 | 11 | 492 |
| 58 | HQ537777_1 | 502 | 1264 |
| 58 | HQ537777_1 | 1266 | 1536 |
| 58 | HQ537777_1 | 1547 | 2157 |
| 58 | HQ537777_1 | 2182 | 2682 |
| 58 | HQ537777_1 | 2753 | 4174 |
| 58 | HQ537777_1 | 4196 | 5638 |
| 58 | HQ537777_1 | 5656 | 5737 |
| 58 | HQ537777_1 | 5741 | 6294 |
| 58 | HQ537777_1 | 6310 | 7776 |
| ORF | M62849_1 | 11 | 1680 |
| ORF | M62849_1 | 1702 | 2677 |
| ORF | M62849_1 | 2678 | 2750 |
| ORF | M62849_1 | 2814 | 3000 |
| ORF | M62849_1 | 3014 | 3984 |
| ORF | M62849_1 | 4063 | 4981 |
| ORF | M62849_1 | 4999 | 7200 |
| ORF | M62849_1 | 7226 | 7786 |
| 16 | NC_001526_2 | 10 | 1869 |
| 16 | NC_001526_2 | 1880 | 2782 |
| 16 | NC_001526_2 | 2783 | 4153 |
| 16 | NC_001526_2 | 4201 | 7865 |
| 59 | X77858_1 | 11 | 706 |
| 59 | X77858_1 | 736 | 2209 |
| 59 | X77858_1 | 2211 | 5247 |
| 59 | X77858_1 | 5266 | 6282 |
| 59 | X77858_1 | 6285 | 7851 |

| HPV Type | GenBank Accession No. | Primary Target Start | Primary Target End |
|---|---|---|---|
| 18 | AY262282_1 | 1 | 7857 |
| 56 | EF177180_1 | 1 | 7845 |
| 45 | EF202166_1 | 1 | 7849 |
| 68b | FR751039_1 | 1 | 7836 |
| 31 | HQ537687_1 | 1 | 7878 |
| 33 | HQ537707_1 | 1 | 7830 |
| 35 | HQ537729_1 | 1 | 7908 |
| 52 | HQ537751_1 | 1 | 7934 |
| 58 | HQ537777_1 | 1 | 7820 |
| ORF | M62849_1 | 1 | 7833 |
| 16 | NC_001526_2 | 1 | 7905 |
| 59 | X77858_1 | 1 | 7896 |

Example 2

Characterization of Isolated DNA

The TrDNA concentration, quality and content obtained after isolating TrDNA from 10 mL of urine from participants with premalignant lesions is shown in Table 3 and from normal participants is shown in Table 4. Specifically, these tables show the DNA concentration (ng/μL), 260/280 ratio as a measure of nucleic acid purity, 260/230 ratio as a secondary measure of nucleic acid purity (Nanodrop, Thermo Fisher Scientific, Waltham, Mass.), and efficiency of DNA isolation (total μg in 30 μL) of TrDNA isolated from women with low grade (n=23) and high grade lesions (n=18) (Table 3) and isolated from 31 normal participants. The mean 260/280 ratio was 1.7 for premalignant samples and 1.4 for normal samples. The mean total TrDNA isolated was 1 μg for premalignant samples and 0.5 μg for normal samples.

An agarose gel of six low grade and six high grade TrRNA DNA samples showed that the isolated TrDNA fraction was enriched for small fragments (FIG. 1A). Another agarose gel of six low grade lesions (LGL), six high grade lesions (HGL), Caski (a cervical cancer cell line that has 600 copies of HPV) and SHIA (a cervical cancer cell line with only 2 HPV copies) also showed enrichment of small fragments (FIG. 1B).

Table 5 shows the comparison between DNA concentration obtained by isolating DNA from urine from the same participants utilizing two different extraction methods, phenol-chloroform (PC) and TrDNA isolation methods (described in Example 1). The extracted TrDNA differed in concentration from genomic DNA extracted from the same participants using the traditional phenol-chloroform extraction method.

Table 6 shows that additional tests using the isolated TrDNA could be performed, such as a global DNA methylation assay (Imprint Methylated DNA Quantification Kit, Sigma-Aldrich, St. Louis, Mo.).

TABLE 3

DNA and efficiency of DNA isolation of TrDNA isolated from women with Low Grade (n = 23) and High Grade Lesions (n = 18).

| SAMPLE | ng/μL | 260/280 | 260/230 | Efficiency (μg) |
|---|---|---|---|---|
| NIE I (Low Grade Lesion) | | | | |
| 454 | 78.5 | 1.87 | 1.45 | 2.36 |
| 455 | 39.4 | 1.67 | 0.83 | 1.18 |
| 456 | 43.5 | 1.61 | 0.72 | 1.31 |
| 457 | 30.9 | 1.55 | 0.69 | 0.93 |
| 460 | 11.7 | 1.2 | 0.28 | 0.35 |
| 461 | 79.2 | 1.77 | 1.39 | 2.38 |
| 511 | 13.1 | 1.54 | 0.65 | 0.39 |
| 513 | 64.1 | 1.98 | 1.61 | 1.92 |
| 514 | 9.7 | 1.43 | 0.51 | 0.29 |
| 515 | 8.8 | 1.67 | 0.51 | 0.26 |
| 519 | 48.7 | 1.86 | 1.44 | 1.46 |
| 524 | 41.5 | 1.55 | 0.61 | 1.25 |
| 545 | 52.6 | 1.96 | 1.75 | 1.58 |
| 552 | 15.1 | 1.82 | 0.64 | 0.45 |
| 554 | 4.5 | 1.59 | 0.49 | 0.14 |
| 555 | 10.8 | 1.72 | 0.86 | 0.32 |
| 556 | 35.4 | 1.86 | 1.43 | 1.06 |
| 557 | 121.2 | 2.07 | 1.7 | 3.64 |
| 558 | 14.9 | 1.47 | 0.51 | 0.45 |
| 561 | 12.4 | 1.61 | 0.79 | 0.37 |
| 565 | 32.4 | 1.75 | 0.63 | 0.97 |
| 570 | 7.6 | 1.42 | 0.58 | 0.23 |
| 575 | 20.9 | 1.35 | 0.42 | 0.63 |
| NIE III (High Grade Lesion) | | | | |
| 212 | 0.7 | 0.38 | 0.07 | 0.02 |
| 240 | 4.8 | 1.55 | 1.13 | 0.14 |
| 253 | 8.3 | 3.27 | 1.23 | 0.25 |
| 259 | 9.1 | 3.99 | 1.63 | 0.27 |
| 296 | 4.9 | 1.11 | 0.21 | 0.15 |
| 299 | 4.2 | 1.05 | 0.4 | 0.13 |
| 445 | 44.5 | 1.49 | 0.46 | 1.34 |
| 447 | 30.9 | 1.78 | 1.83 | 0.93 |
| 448 | 18.7 | 1 | 0.29 | 0.56 |
| 449 | 81.4 | 1.76 | 1.19 | 2.44 |
| 481 | 25.3 | 1.49 | 0.57 | 0.76 |
| 504 | 37 | 1.67 | 0.83 | 1.11 |
| 512 | 16.2 | 1.57 | 0.49 | 0.49 |
| 551 | 38.1 | 1.86 | 0.96 | 1.14 |
| 563 | 37.6 | 1.23 | 0.36 | 1.13 |

TABLE 3-continued

DNA and efficiency of DNA isolation of TrDNA isolated from women with Low Grade (n = 23) and High Grade Lesions (n = 18).

| SAMPLE | ng/μL | 260/280 | 260/230 | Efficiency (μg) |
|---|---|---|---|---|
| 571 | 21.7 | 1.55 | 0.57 | 0.65 |
| 577 | 6 | 1.09 | 0.36 | 0.18 |
| 581 | 214.7 | 1.89 | 1.96 | 6.4 |

TABLE 4

DNA Concentration of TrDNA isolated from 31 normal participants. TrDNA Normal Cohort

| SAMPLE | ng/μL | 260/280 | 260/230 | Efficiency (μgs) |
|---|---|---|---|---|
| 10403 | 32.64 | 1.37 | 0.5 | 0.98 |
| 58560 | 24.22 | 1.8 | 0.42 | 0.73 |
| 91765 | 23.87 | 1.19 | 0.25 | 0.72 |
| 94851 | 40.85 | 1.43 | 0.52 | 1.23 |
| 101753 | 30.81 | 1.49 | 0.52 | 0.92 |
| 117139 | 39.35 | 1.07 | 0.28 | 1.18 |
| 231469 | 5.78 | 1.23 | 0.24 | 0.17 |
| 278816 | 23.86 | 1.34 | 0.4 | 0.72 |
| 278816 | 23.86 | 1.34 | 0.4 | 0.72 |
| 295210 | 4.34 | 1.76 | 0.29 | 0.13 |
| 297229 | 10.76 | 1.29 | 0.34 | 0.32 |
| 305415 | 20.45 | 1.23 | 0.29 | 0.61 |
| 338542 | 31.46 | 1.44 | 0.77 | 0.94 |
| 392736 | 7.03 | 1.38 | 0.42 | 0.21 |
| 417946 | 30.31 | 1.55 | 0.43 | 0.91 |
| 436991 | 16.67 | 1.19 | 0.24 | 0.50 |
| 438652 | 9.11 | 1.39 | 0.3 | 0.27 |
| 443755 | 9.27 | 1.3 | 0.26 | 0.28 |
| 493850 | 9.91 | 1.37 | 0.36 | 0.30 |
| 499368 | 23.61 | 1.49 | 0.45 | 0.71 |
| 594099 | 9.42 | 1.59 | 0.29 | 0.28 |
| 60933 | 7.73 | 1.27 | 0.26 | 0.23 |
| 752848 | 13.91 | 1.26 | 0.33 | 0.42 |
| 880113 | 10.2 | 2.24 | 0.29 | 0.31 |
| 883139 | 24.12 | 1.61 | 0.53 | 0.72 |
| 889527 | 5.46 | 1.49 | 0.42 | 0.16 |
| 911250 | 11.86 | 1.23 | 0.29 | 0.36 |
| 233408 | 13.88 | 1.38 | 0.36 | 0.42 |
| 315106 | 8.76 | 1.26 | 0.21 | 0.26 |
| 893778 | 4.4 | 1.7 | 0.27 | 0.13 |
| 855471 | 5.9 | 1.5 | 0.29 | 0.18 |

TABLE 5

Comparison between DNA concentrations obtained by isolating DNA from urine from the same participants utilizing two different extraction methods: Phenol Chloroform (PC) and Tr-DNA isolation methods.

| Sample ID | PC ng/μL | Tr-DNA ng/μL |
|---|---|---|
| 301539 | 338.56 | 52.8 |
| 338542 | 887.38 | 31.46 |
| 10403 | 223.98 | 32.64 |
| 117139 | 206.46 | 39.35 |
| 381022 | 319.55 | 21.28 |
| 693696 | 369.83 | 37.17 |

TABLE 6

Global DNA methylation levels quantified in TrDNA isolated from normal participants.

| Sample | Global DNA Methylation % |
|---|---|
| 392736 | 22.3 |
| 883139 | 17.7 |
| 594099 | 17.9 |
| 889527 | 18.7 |
| 101753 | 18.7 |
| 58560 | 18.0 |
| 233408 | 16.0 |
| 417946 | 16.6 |
| 499368 | 15.9 |
| 278816 | 19.8 |
| 436991 | 23.4 |
| 733942 | 21.8 |

Example 3

HPV-Targeted Enrichment and Sequence Analysis from HeLa (HPV 18) and CSCC7 (HPV16) Cell Lines HPV infected cell lines, HeLa (HPV18) and CSCC7 (HPV16), were successfully processed for SEQCAP HPV-targeted enrichment and sequence analysis. 250 ng genomic DNA was fragmented by nebulization and barcoded sequencing adaptors were ligated to polished ends. Following purification, a modified NimbleGen SEQCAP protocol was followed to enrich for HPV sequences from the host genomic DNA. This modified protocol allowed samples to be run with a lower amount (as low as 100 nanograms) of the recommended input DNA (1 ug). Two rounds of selection were performed. FIGS. 2A-2B show BioAnalyzer profiles of the purified, HPV-enriched DNA following each round of sequence capture.

To assess performance of the SEQCAP enrichment, real time quantitative PCR utilizing SYBR green detection of an HPV-specific assay (XEN-HPV) was performed with the purified, HPV-enriched DNA in comparison to pre-capture template and genomic control DNA. Quantitation was performed on both pre-capture and post-capture samples using the Quant-iT PicoGreen dsDNA reagent kit (Invitrogen, Life Technologies, Carlsbad, Calif.) and a normalized amount of DNA (5 ng) was analyzed. This method employs an ultra-sensitive fluorescent nucleic acid stain.

FIG. 3 is an amplification plot demonstrating the successful amplification and enrichment of HPV during the SEQCAP protocol. Delta CT values for HeLa and CSCC7 were 14.88 and 12.66, respectively. Based on an estimated efficiency for the assay, approximate fold enrichments are greater than 1700.

Following a calculation and normalization to 1×E09 molecules per microliter, both samples were pooled and processed for sequence analysis. Standard protocols for the GS Junior Titanium system (Roche, Basel, CH) were followed (emPCR amplification method, Lib-L, and sequencing method). Enrichment recovery percentage was approximately 20%. 500,000 beads were processed for the sequencing run.

QC metrics of the sequence run were as follows: the total number of Pass Filter sequence reads was 100,428 and the total number of bases was over 41 million. The sequence read length average for TrDNAs was 130.3 bp. For preliminary analysis, alignments to reference sequences for both HPV 16 and 18 were performed using the GS Reference Mapper software (Roche, Basel, CH). 91.63% of reads mapped to the reference HPV sequences, with the total number of mapped base pairs over 36 million (88%). The number of fully mapped reads was 14,899 (14.84%), and the number of partially mapped reads was 70,686 (88.17%). The average coverage of reference was 78% for HPV18 in the CSCC7 DNA, 86% for HPV16 in HeLa DNA, as well as, 100% for HPV18 and 96% for HPV16 in TrDNA samples. Only ~7% of reads were unmapped. Consensus accuracy was >99%. Representation of barcodes was balanced with 51,952 reads for HeLa vs 48,095 for CSCC7.

Sequence libraries were also prepared from 500 ng and 100 ng HeLA DNA to assess the sensitivity and robustness of the capture protocol. Yields of post-$2^{nd}$ capture HPV-enriched DNA were very similar at all concentrations, showing that this protocol works well for samples of limiting quantity, such as TrDNA samples.

Example 4

HPV-Targeted Enrichment and Sequence Analysis of TrDNAs 455 and 456 and Super-Fragmented Cell Line CSCC7

A modified NimbleGen SEQCAP protocol was followed to enrich for HPV sequences from TrDNAs 455 and 456, and super-fragmented cell line CSCC7. Two rounds of selection were performed. Following purification of Post-$2^{nd}$ capture LM-PCR reactions, DNA quality was assessed by High Sensitivity DNA Lab Chip analysis on the BioAnalyzer 2100 (Agilent Life Technologies, Santa Clara, Calif.), and quantity of DNA yield determined by PicoGreen Fluorescent assay (Life Technologies, Carlsbad, Calif.). As seen in FIGS. 4A-4B, resulting DNA profiles were similar in size range for the TrDNA samples (range in by on X axis). Concentrations and yields were more variable, but were ample for subsequent qPCR and sequencing.

An assessment of the SEQCAP enrichment was performed by real time quantitative PCR using the TrDNA-HPV SYBR green assay. This included the purified, HPV-enriched DNA ("Post-Capture LM-PCR") in comparison to Precapture LM-PCR and genomic control DNAs. The average Ct value for Pre-Capture LM-PCR DNAs was 35.74. The average Ct value for Post-Capture LM-PCR DNAs (TrDNA 455 and cell line CSCC7) was 19.73; therefore the Delta Ct value was 16.01. Based on an estimated efficiency for the assay, the approximate fold enrichment was greater than 12,000. TrDNA 456 Post-Capture LM-PCR did not amplify for this assay; however, numbers of molecules per microliter were calculated for both TrDNA samples and the yields for both were ample for sequencing. Appropriate dilutions, 1×E09 molecules per microliter, and pools were made for HPV-enriched TrDNAs 455 and 456, and the processing for Next Generation Sequencing on the Roche 454 platform performed (GS Junior Titanium Lib-L emPCR amplification adapted for short fragments and Sequencing methods).

The sequencing methods used with the post-SEQCAP TrDNA samples were optimized previously for sequencing runs with small fragment, aptamer samples (FIGS. 5 and 6). FIG. 4 shows the size profile of a short fragment template processed for sequencing on the Roche GS Junior System. A library was prepared by ligation of bar-coded adaptors, and subsequently pooled with another bar-coded library, clonally amplified by emulsion PCR, and sequenced. FIG. 5 shows a read length QC profile of pooled small fragments sequenced on the Roche GS Junior System. The QC metrics for sequencing on the Roche GS Junior System included Raw Wells number, Key Pass Wells number, Passed Filter Wells number, and Percent Pass Filter. Averages for these values from previous short fragment runs performed were 160,882 Raw Wells, 150,244 Key Pass Wells, 116,852 Passed Filter Wells and 78% Passed Filter wells. All exceeded manufacturer's specifications.

In this Example, the amplicon pipeline for signal processing was used, and preliminary analysis of the sequencing run was performed with GS Run Browser. There were 101,172 Pass Filter sequence reads, and the read count was balanced between barcodes. Percentages of reference mapping and coverage were similar to the previous run. Amplification plots are shown in FIGS. 7A-7B.

Example 5

HPV-Targeted Enrichment and Sequence Analysis of TrDNAs 445, 481, 504, 513, and 571

Five additional TrDNAs were selected for Sequence Capture and sequencing. All had a "good" quality profile when assessed on the BioAnalyzer as determined by a size range below about 250 bp, and most (4) had a positive Ct value when assessed by real time quantitative PCR for the TrDNA-HPV SYBR green assay. Input amounts of TrDNA to the Rapid Library Preparation protocol were variable. For one sample, 100 ng was used. Approximately 50 ng was used for 3 samples, and for one sample, less than 25 ng was used. As in the previous runs, barcoded adaptors were ligated onto polished DNA ends. Following purification, the modified NimbleGen SEQCAP protocol with two rounds of selection was followed to enrich for HPV sequences. Assessment of the SEQCAP enrichment was performed by real-time quantitative PCR using the TrDNA-HPV SYBR green assay, with the purified, HPV enriched DNA ("Post-Capture LM-PCR") being compared to the Pre-Capture LM-PCR and genomic control DNAs (FIGS. 6 and 7). Based on an estimated efficiency for the assay, the approximate average fold enrichment was greater than 300. Yields from all five were ample for sequencing. Results are shown in FIG. 8.

Example 6

HPV-Targeted Enrichment and Sequence Analysis of TrDNAs 445, 455, 456, 481, 504, 513, and 571

TrDNA samples were analyzed for high risk HPV DNA using the HPV TrDNA SYBR green qPCR assay. FIGS. 9A-9B show amplification plots of real-time quantitative PCR utilizing SYBR green detection of the HPV-specific assay (HPV-TrDNA SYBR assay). Results are shown for TrDNA from women with low grade and high grade premalignant cervical lesions and normal cervical epithelium. HeLa genomic DNA, DNA from a cervical cancer cell line, was included as a positive control. Ct ranges were variable in the TrDNA samples, but were in a similar range as the genomic control. Most Control TrDNA samples were negative for the assay.

For sequence capture next generation sequencing, the total number of Pass Filter sequence reads for TrDNA samples was 230,385, the total number of bases over 32 million, and the read length average 138.3 bp. Coverage of the reference sequences (HPV18 and HPV16) was achieved for all TrDNA samples sequenced (range: 73%-100%). The range of percent mapped reads per sample was 28.8% to 98%. The average coverage of reference sequences was 78% for HPV18 in the CSCC7 DNA and 86% for HPV16 in HeLa DNA, as well as 100% for HPV18 and 96% for HPV16 in TrDNA samples.

For the HPV TrDNA dual sequence capture approach, a custom-designed pool of HPV-specific dual sequence capture probes was used for library amplification and target selection in TR-DNAs (NimbleGen SeqCap EZ Choice Library). Using the SYBR green qPCR assay, an HPV E1 region common to thirteen high-risk HPV types was amplified. The average Delta Ct value for Pre-Capture vs. Post-Capture LM-PCR DNAs was 11.07, corresponding to an average fold enrichment of 670 (FIG. 3).

The amplified HPV TrDNA was then sequenced and the genome was assembled. Table 7 shows alignment results against HPV16 and HPV18 reference genomes for seven HPV TrDNA samples and two cervical cancer samples sequenced after dual sequence capture.

TABLE 7

Alignment results against HPV16 and HPV18 reference genomes

| Sample ID | Lesion | Input DNA (ng) | # Sequence Reads | HPV16ref | | | HPV18ref | | |
|---|---|---|---|---|---|---|---|---|---|
| | | | | # Unique Match Reads | % of All Reads | % Coverage | # Unique Match Reads | % of All Reads | % Coverage |
| TrDNA 445 | CIN2-3 | 60 | 25998 | 24670 | 95 | 100 | 722 | 3 | 73.4 |
| TrDNA 455 | CIN-1 | 100 | 55002 | 144 | 0.3 | 81.6 | 53075 | 96.5 | 100 |
| TrDNA 456 | CIN-1 | 100 | 45982 | 953 | 2.1 | 91.4 | 1647 | 3.6 | 74.3 |
| TrDNA 481 | CIN2-3 | 55 | 18159 | 6700 | 37 | 100 | 1185 | 6.5 | 87.1 |
| TrDNA 504 | CIN2-3 | 60 | 33218 | 11227 | 33.8 | 99.4 | 4624 | 13.9 | 100 |
| TrDNA 513 | CIN-1 | <30 | 25242 | 5085 | 20.1 | 100 | 2202 | 8.7 | 100 |
| TrDNA 571 | CIN2-3 | 100 | 26472 | 12229 | 46 | 100 | 3989 | 15.1 | 100 |
| Average | | 72 | 32868 | 8715 | 33 | 96 | 9635 | 21 | 91 |
| HeLa | cancer | 250 | 51952 | Cervical cancer cell line with HPV18 | | | 46284 | 89.1 | 67.07 |
| CSCC7 | cancer | 250 | 48095 | 44262 | 92 | 76.6 | Cervical cancer cell line with HPV16 | | |

To determine the dominant HPV types in the TrDNA samples after dual sequence capture, sim4db, a utility for fast batch spliced alignment (Walenz and Florea, 2011), was used to match reads to a combined file containing 21 high risk (16, 18, 31, 33, 35, 39, 45, 52, 56, 58, 59 and 68b) and low risk (6, 11, 42, 44, 53, 54, 61, 72, and 81) HPV reference sequences (NCBI listing of HPV genome projects). In each sample, some number of reads remained unmapped. The unmapped numbers were negligible for samples 445 and 455, but quite significant for others (samples 456, 481, 504, 513). They probably represented less common HPV types or human sequences. Representative types per sample followed the expected distribution (mostly 16 and 18; Table 8).

TABLE 8

Dominant HPV Types in the TrDNA Samples

| TrDNA_445 CIN 2-3 | HPV16 |
| TrDNA_455 CIN 1 | HPV18 |
| TrDNA_456 CIN 1 | HPV58, HPV33, HPV59 |
| TrDNA_481 CIN 2-3 | HPV16, HPV18 |

TABLE 8-continued

Dominant HPV Types in the TrDNA Samples

| TrDNA_504 CIN 2-3 | HPV16, HPV18, HPV58-like* |
| TrDNA_513 CIN 1 | HPV16, HPV18, HPV53, HPV56-like* |
| TrDNA_571 CIN 2-3 | HPV16, HPV18 |

*low (80-85%) percent sequence identity

Detailed analysis of TrDNA_445 CIN 2-3 and TrDNA_456 CIN 1 can be seen in FIG. 10. Most of the contigs contained very few reads, in the tens to hundreds for most types, except HPV59, HPV33 and HPV58. The assembly for HPV16 and HPV18 had low coverage. This sample seemed to be a medley of HPV strains.

FIGS. 11A-11B show a large scale (8 Kb) view (FIG. 11A) and close-up (1 Kb) view (FIG. 11B) of multiple genome-wide pairwise alignments of four high risk HPV types (18, 31, 45, 52) and five low risk HPV types (6, 11, 42, 53, 54) and seven HPV TrDNA samples against the HPV 16 reference genome.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Benson D. A.; Karsch-Mizrachi I.; Lipman D. J.; Ostell J.; Sayers E. W. (2009). GenBank. *Nucleic Acids Res.* 2009 January; 37 (Database issue):D26-31. Epub 2008 Oct. 21.

Beaudenon, S.; Huibregtse, J. M., HPV E6, E6AP and cervical cancer. *BMC Biochem* 9 Suppl 1, S4 (2008).

Blanchette, M.; Kent, W. J.; Riemer, C.; Elnitski, L.; Smit, A. F.; Roskin, R. M.; Baertsch, R.; Rosenbloom, K.; Clawson, H.; Green, E. D.; Haussler, D.; Miller, W. (2004) Aligning multiple genomic sequences with the threaded blockset aligner, *Genome Res.* 14(4), 708-15.

Brown, A. J. and C. L. Trimble, New technologies for cervical cancer screening. Best Pract Res Clin Obstet Gynaecol, 2012. 26(2): p. 233-42.

Cuschieri, K. S.; Whitley, M. J.; Cubie, H. A. Human papillomavirus type specific DNA and RNA persistence—implications for cervical disease progression and monitoring. *J Med Virol* 2004.73, 65.

Dehn, D.; Torkko, K. C.; Shroyer, K. R. Human papillomavirus testing and molecular markers of cervical dysplasia and carcinoma. *Cancer* 2007. 111, 1.

Dillner, J.; Rebolj, M.; Birembaut, P.; Petry, K.-U.; Szarewski, A.; Munk, C.; de Sanjose, S.; Naucler, P.; Lloveras, B.; Kjaer, S.; Cuzick, J.; van Ballegooijen, M.; Clavel, C.; Iftner, T.; Long term predictive values of cytology and human papillomavirus testing in cervical cancer screening: joint European cohort study. *BMJ,* 2008. 337: p. a1754.

Doorbar, J., Molecular biology of human papillomavirus infection and cervical cancer. Clin Sci (Lond), 2006. 110(5): p. 525-41.

Eberharter, A. and P. B. Becker, Histone acetylation: a switch between repressive and permissive chromatin. Second in review series on chromatin dynamics. *EMBO Rep,* 2002. 3(3): p. 224-9.

Esteller, M. Epigenetics provides a new generation of oncogenes and tumour-suppressor genes. Br J Cancer, 2006. 94(2): p. 179-83.

Florea, L.; McClelland, M.; Riemer, C.; Schwartz, S. and Miller, W. Enterix 2003: Visualization Tools for Genome Alignments of Enterobacteriaceae, *Nucl. Acids Res.* 2003. 31(13), 3527-32.

Kjaer, S. K.; van den Brule, A. J. C.; Paull, G.; Svare, E. I.; Sherman, M. E.; Thomsen, B. L.; Suntum, M.; Bock, J. E.; Poll, P. A.; Meijer, C. J. L. M. Type specific persistence of high risk human papillomavirus (HPV) as indicator of high grade cervical squamous intraepithelial lesions in young women: population based prospective follow up study. *BMJ* 2002. 325, 572.

Melkonyan, H. S., Feaver, W. J.; Meyer, E.; Scheinker, V.; Shekhtman, E. M.; Xin, Z.; Umansky, S. R. Transrenal nucleic acids: from proof of principle to clinical tests. *Ann N Y Acad Sci,* 2008. 1137: p. 73-81.

Monsonego, J.; Bosch, F. X.; Coursaget, P.; Cox, Franco, E.; Frazer, I.; Sankaranarayanan, R.; Schiller, J.; Singer, A.; Wright, T. C. Jr.; Kinney, W.; Meijer, C. J.; Linder, J.; McGoogan, E.; Meijer, C. Cervical cancer control, priorities and new directions. *Int J Cancer* 2004. 108, 329.

Sasagawa, T., [Updated cervical cancer screening; human papilloma virus and Papanicolaou tests]. Rinsho Byori, 2009. 57(9): p. 905-12.

Saslow, D.; Solomon, D.; Lawson, H. W.; Killackey, M.; Kulasingam, S. L.; Cain, J.; Garcia, F. A. R.; Moriarty, A. T.; Waxman, A. G. Wilbur, D. C.; Wentzensen, N.; Downs, L. S.; Spitzer, M.; Moscicki, A.-B.; Franco, E.-L.; Stoler, M.-H.; Schiffman, M.; Castle, P. E.; Myers, E. R.; American Cancer Society, American Society for Colposcopy and Cervical Pathology, and American Society for Clinical Pathology screening guidelines for the prevention and early detection of cervical cancer. *CA Cancer J Clin* 2012. 62(3): p. 147-72. Sayers E. W.; Barrett, T.; Benson D. A.; Bryant S. H.; Canese K.; Chetvernin V.; Church D. M.; DiCuccio M.; Edgar R.; Federhen S.; Feolo M.; Geer L. Y.; Helmberg W.; Kapustin Y.; Landsman D.; Lipman D. J.; Madden T. L.; Maglott D. R.; Miller V.; Mizrachi I.; Ostell J.; Pruitt K. D.; Schuler G. D.; Sequeira E.; Sherry S. T.; Shumway M.; Sirotkin K.; Souvorov A.; Starchenko G.; Tatusova T. A.; Wagner L.; Yaschenko E.; Ye J. (2009). Database resources of the National Center for Biotechnology Information. *Nucleic Acids Res.* 2009 January; 37(Database issue):D5-15. Epub 2008 Oct. 21.

Schwartz, S.; Kent, W. J.; Smit, A.; Zhang, Z.; Baertsch, R.; Hardison, R. C.; Haussler, D.; Miller, W. Human-Mouse Alignments with Blastz, *Genome Res.* 2003. 3(1), 103-7.

Schwartz, S.; Zhang, Z.; Frazer, K. A.; Smit, A.; Riemer, C.; Bouck, J.; Gibbs, R.; Hardison, R.; W. Miller, W. PipMaker—A web server for aligning two genomic DNA sequences, *Genome Res.* 2000. 10(4), 577-86.

Studnicki, J., Berndt, D. J. Luther, S. L.; Fisher, J. W.; van Caulil, K.; Brennan, M. J.; Martinez, Y. G.; Clarke, P. Hispanic health status in Orange County, Fla. *J Public Health Manag Pract* 2005. 11(4): p. 326-32.

Tycko, B., Epigenetic gene silencing in cancer. *J Clin Invest* 2000. 105(4): p. 401-7.

Walenz, B., Florea, L. Sim4db and leaff: Utilities for fast batch spliced alignment and sequence indexing", *Bioinformatics* 2011. 27(13):1869-70.

Woodman, C. B., Collins, S. I.; Young, L. S. The natural history of cervical HPV infection: unresolved issues. *Nat Rev Cancer* 2007. 7(1): p. 11-22.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A sequence-based method for detecting HPV Trans-Renal DNA (TrDNA) in a subject, the method comprising:
   (a) isolating one or more low molecular weight, fragmented cell-free nucleic acids from a urine sample from a subject thereby creating a library of the low molecular weight, fragmented cell-free nucleic acids;
   (b) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises:
      (i) amplifying the HPV TrDNA in the library using ligation-mediated PCR (LM-PCR) to form a pre-capture PCR library;
      (ii) hybridizing the pre-capture PCR library to a pool of HPV-specific capture probes specific for the HPV E1 region of the following HPV subtypes selected from the group consisting of: HPV16, 18, 31, 33, 35, 39, 45, 51, 52, 56, 58, 59 and 68, to form a post-capture PCR library;
      (iii) amplifying the post-capture PCR library to produce one or more enriched HPV TrDNA; and
      (iv) optionally repeating steps (iii) and (iv);
   (d) adding at least one index to the one or more enriched HPV TrDNA;
   (e) performing multiplexed sequencing of the one or more enriched HPV TrDNA having at least one index added thereto to produce a multiplexed nucleotide sequence;
   (f) performing a sequence alignment between the multiplexed nucleotide sequence and the nucleotide sequence of one or more known HPV genotypes; and
   (g) determining the percentage sequence identity between the multiplexed nucleotide sequence and the nucleotide sequence of the one or more known HPV genotypes; wherein at least a 60% sequence identity between the multiplexed nucleotide sequence and the nucleotide sequence of the one or more known HPV genotypes means that HPV TrDNA has been detected in the subject.

2. The method of claim 1, further comprising performing quantitative PCR (qPCR) to amplify the one or more enriched HPV TrDNA.

3. The method of claim 2, wherein amplifying the one or more enriched HPV TrDNA amplifies the E1 region of at least one HPV genotype.

4. The method of claim 2, wherein amplifying the one or more enriched HPV TrDNA amplifies most or all of the genotype-specific regions of at least one HPV genome.

5. The method of claim 1, wherein the low molecular weight, fragmented cell-free nucleic acids are from about 150 to about 250 base pairs.

6. The method of claim 1, wherein isolating the one or more low molecular weight, fragmented cell-free nucleic acids from the urine sample occurs by separating the nucleic acids from the urine by applying the nucleic acids to a container comprising Q-Sepharose and/or silica resin substrate, allowing the nucleic acids to bind to the substrate, washing the substrate, and then eluting the nucleic acids with an elution buffer.

7. The method of claim 1, wherein the subject is human.

8. The method of claim 1, wherein the method is for detecting methylated HPV Trans-Renal DNA (TrDNA) in a subject, and wherein prior to step (d) the post-capture library is treated with a bisulfite compound and is amplified using PCR to form one or more amplified methylated HPV TrDNA; and further wherein at least a 70% sequence identity between the multiplexed nucleotide sequence and the nucleotide sequence of the one or more known methylated HPV genotypes means that methylated HPV TrDNA has been detected in the subject.

9. A sequence-based method for predicting or screening for cancer by detecting high-risk HPV Trans-Renal DNA (TrDNA) in a subject, the method comprising:
   (a) isolating one or more low molecular weight, fragmented cell-free nucleic acids from a urine sample from a subject thereby creating a library of the low molecular weight, fragmented cell-free nucleic acids;
(b) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises:
  (i) amplifying the HPV TrDNA in the library using ligation-mediated PCR (LM-PCR) to form a pre-capture PCR library;
  (ii) hybridizing the pre-capture PCR library to a pool of HPV-specific capture probes specific for the HPV E1 region of the following HPV subtypes selected from the group consisting of: HPV16, 18, 31, 33, 35, 39, 45, 51, 52, 56, 58, 59 and 68, to form a post-capture PCR library;
  (iii) amplifying the post-capture PCR library to produce one or more enriched HPV TrDNA; and
  (iv) optionally repeating steps (iii) and (iv);
(d) adding at least one index to the one or more enriched HPV TrDNA;
(e) performing multiplexed sequencing of the one or more enriched HPV TrDNA having at least one index added thereto to produce a multiplexed nucleotide sequence;
(f) performing a sequence alignment between the multiplexed nucleotide sequence and the nucleotide sequence of one or more known HPV genotypes; and
(g) determining the percentage sequence identity between the multiplexed nucleotide sequence and the nucleotide sequence of the one or more known HPV genotypes;
wherein at least a 60% sequence identity between the multiplexed nucleotide sequence and the nucleotide sequence of the one or more known high-risk HPV genotypes is indicative that the subject has or is at risk for developing a cancer.

10. The method of claim 9, wherein the low molecular weight, fragmented cell-free nucleic acids are from about 150 to about 250 base pairs.

11. The method of claim 9, wherein the cancer is selected from the group consisting of cervical, anal, penile, and oropharyngeal.

12. The method of claim 9, wherein isolating the one or more low molecular weight, fragmented cell-free nucleic acids from the urine sample occurs by separating the nucleic acids from the urine by applying the nucleic acids to a container comprising Q-Sepharose and/or silica resin substrate, allowing the nucleic acids to bind to the substrate, washing the substrate, and then eluting the nucleic acids with an elution buffer.

13. The method of claim 9, wherein the subject is human.

14. The method of claim 9, wherein the method is for predicting or screening for cancer by detecting high-risk methylated HPV Trans-Renal DNA (TrDNA) in a subject, and wherein prior to step (d) the post-capture library is treated with a bisulfate compound and is amplified using PCR to form one or more amplified methylated HPV TrDNA; and further wherein at least a 70% sequence identity between the multiplexed nucleotide sequence and the nucleotide sequence of the one or more known high-risk methylated HPV genotypes is indicative that the subject has or is at risk for developing a cancer.

15. A method for detecting methylated human Trans-Renal DNA (TrDNA) in a subject, the method comprising:
(a) isolating one or more low molecular weight, fragmented cell-free nucleic acids from a urine sample from a subject thereby creating a library of the low molecular weight, fragmented cell-free nucleic acids;
(b) enriching the one or more low molecular weight fragmented cell-free nucleic acids isolated from the urine sample for HPV TrDNA using a high-risk HPV-specific solution-based capture method to enrich the HPV genome to produce one or more enriched HPV TrDNA, wherein enriching the one or more low molecular weight fragmented cell-free nucleic acids comprises:
  (i) amplifying the HPV TrDNA in the library using ligation-mediated PCR (LM-PCR) to form a pre-capture PCR library;
  (ii) hybridizing the pre-capture PCR library to a pool of HPV-specific capture probes specific for the HPV E1 region of the following HPV subtypes selected from the group consisting of: HPV16, 18, 31, 33, 35, 39, 45, 51, 52, 56, 58, 59 and 68, to form a post-capture PCR library;
  (iii) amplifying the post-capture PCR library to produce one or more enriched HPV TrDNA; and
  (iv) optionally repeating steps (iii) and (iv);
(d) adding at least one index to the one or more enriched human TrDNA;
(e) performing multiplexed sequencing of the one or more enriched human TrDNA having at least one index added thereto to produce a multiplexed nucleotide sequence;
(f) performing a sequence alignment between the multiplexed nucleotide sequence and the nucleotide sequence of the human genome; and
(g) determining the percentage sequence identity between the multiplexed nucleotide sequence and the nucleotide sequence of the human genome;
wherein prior to step (d) the post-capture library is treated with a bisulfite compound and is amplified using PCR to form one or more amplified methylated human TrDNA; and further wherein at least a 60% sequence identity between the multiplexed nucleotide sequence and the nucleotide sequence of the human genome means that methylated human TrDNA has been detected in the subject.

* * * * *

UNITED STATES PATENT AND TRADEMARK OFFICE
CERTIFICATE OF CORRECTION

| | |
|---|---|
| PATENT NO. | : 9,809,864 B2 |
| APPLICATION NO. | : 14/772004 |
| DATED | : November 7, 2017 |
| INVENTOR(S) | : Rafael Guerrero Preston, Anne Jedlicka and David Sidransky |

Page 1 of 1

It is certified that error appears in the above-identified patent and that said Letters Patent is hereby corrected as shown below:

In the Specification

Column 1, delete Lines 16-23 and insert:

--STATEMENT OF GOVERNMENTAL INTEREST
This invention was made with government support under grant numbers CA164092, CA084986, CA086402, awarded by the National Institutes of Health. The government has certain rights in the invention.--

Signed and Sealed this
Thirtieth Day of January, 2018

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 10

<210> SEQ ID NO 1
<211> LENGTH: 69
<212> TYPE: DNA
<213> ORGANISM: Human papillomavirus type 16

<400> SEQUENCE: 1
caataattca tctataaaac taaccccta acccaaatcc cttcaaccca aacccttac    60

```
tataaaacc                                                                     69

<210> SEQ ID NO 2
<211> LENGTH: 151
<212> TYPE: DNA
<213> ORGANISM: Human papillomavirus type 16

<400> SEQUENCE: 2
acacatttta tccaccaaaa cacaactcca atgtttcacc acccacacca cccacccaca            60
aacttaccac acttatccac acacctccaa acaactatac atcatataat attacvaatc           120
tctctactcc aaccaacact tactcccacc t                                          151

<210> SEQ ID NO 3
<211> LENGTH: 301
<212> TYPE: DNA
<213> ORGANISM: Human papillomavirus type 16

<400> SEQUENCE: 3
cacctatatc actttccttt tccccattta tccatactat atacacatcc caatccatat            60
cctctatctc ataaatcttt aaacttttat tctaaaatta ctcactatac acattattct           120
tatactttct atccaacaac attacaacac caatacaaca aacccttctc tcatttctta           180
attacctcta ttaactctca aaacccactc tctcctcaac aaaaccaaac acatctccac           240
aaaaaccaaa cattccataa tataaccct ccctccaccc ctccatctat ctcttcttcc            300
a                                                                           301

<210> SEQ ID NO 4
<211> LENGTH: 23
<212> TYPE: DNA
<213> ORGANISM: Human papillomavirus type 16

<400> SEQUENCE: 4
acctacacaa acccacctct aat                                                    23

<210> SEQ ID NO 5
<211> LENGTH: 56
<212> TYPE: DNA
<213> ORGANISM: Human papillomavirus type 16

<400> SEQUENCE: 5
catccatcca catacaccta cattccatca atatatctta catttccaac cacaca               56

<210> SEQ ID NO 6
<211> LENGTH: 50
<212> TYPE: DNA
<213> ORGANISM: Human papillomavirus type 16

<400> SEQUENCE: 6
caactcatct ctactcttat caccaattaa atcacacctc acaccaccac                      50

<210> SEQ ID NO 7
<211> LENGTH: 14
<212> TYPE: DNA
<213> ORGANISM: Human papillomavirus type 16

<400> SEQUENCE: 7
catcaaatac atcc                                                              14

<210> SEQ ID NO 8
<211> LENGTH: 63
```

```
<212> TYPE: DNA
<213> ORGANISM: Human papillomavirus type 16

<400> SEQUENCE: 8
tccacctcca caaccacaac cccacacacc ccattacaat attctaacct tttcttccaa      60
ctc                                                                   63

<210> SEQ ID NO 9
<211> LENGTH: 11
<212> TYPE: DNA
<213> ORGANISM: human papillomavirus

<400> SEQUENCE: 9
acactccaac c                                                          11

<210> SEQ ID NO 10
<211> LENGTH: 19
<212> TYPE: DNA
<213> ORGANISM: human papillomavirus

<400> SEQUENCE: 10
acttaatcat caacattta                                                  19
```